(12) United States Patent
Rollend et al.

(10) Patent No.: US 10,013,599 B2
(45) Date of Patent: Jul. 3, 2018

(54) FACE DETECTION, AUGMENTATION, SPATIAL CUEING AND CLUTTER REDUCTION FOR THE VISUALLY IMPAIRED

(71) Applicant: The Johns Hopkins University, Baltimore, MD (US)

(72) Inventors: Derek M. Rollend, Baltimore, MD (US); Kapil D. Katyal, Chevy Chase, MD (US); Kevin C. Wolfe, Lutherville, MD (US); Dean M. Kleissas, Washington, DC (US); Matthew P. Para, Laurel, MD (US); Paul E. Rosendall, Olney, MD (US); John B. Helder, Columbia, MD (US); Philippe M. Burlina, N. Bethesda, MD (US); Duane C. Cornish, Collegeville, PA (US); Ryan J. Murphy, Columbia, MD (US); Matthew S. Johannes, Catonsville, MD (US); Arup Roy, Santa Clarita, CA (US); Seth D. Billings, Bethesda, MD (US); Jonathan M. Oben, Bowie, MD (US); Robert J. Greenberg, Los Angeles, CA (US)

(73) Assignee: The Johns Hopkins University, Baltimore, MD (US)

( * ) Notice: Subject to any disclaimer, the term of this patent is extended or adjusted under 35 U.S.C. 154(b) by 24 days.

(21) Appl. No.: 15/206,453

(22) Filed: Jul. 11, 2016

(65) Prior Publication Data
US 2017/0017831 A1    Jan. 19, 2017

Related U.S. Application Data

(60) Provisional application No. 62/308,204, filed on Mar. 14, 2016, provisional application No. 62/191,780, filed on Jul. 13, 2015.

(51) Int. Cl.
*G06K 9/00* (2006.01)
*G06T 5/40* (2006.01)
(Continued)

(52) U.S. Cl.
CPC ..... *G06K 9/00228* (2013.01); *A61N 1/36046* (2013.01); *G06F 1/163* (2013.01);
(Continued)

(58) Field of Classification Search
None
See application file for complete search history.

(56) References Cited

U.S. PATENT DOCUMENTS

| 7,979,134 B2 * | 7/2011 | Chow | A61N 1/0543 607/54 |
| 9,569,657 B2 * | 2/2017 | Talbot | G06K 9/00228 |

(Continued)

OTHER PUBLICATIONS

Kiral-Kornek et al. "Improved visual performance in letter perception through edge orientation encoding in a retinal prosthesis simulation", Journal of Neural Engineering, vol. 11, No. 6, Published Oct. 13, 2014, Available online at: http://iopscience.iop.org/article/10.1088/1741-2560/11/6/066002/meta.*

(Continued)

*Primary Examiner* — Tahmina Ansari
(74) *Attorney, Agent, or Firm* — Todd R. Farnsworth

(57) ABSTRACT

An apparatus for improving performance of a retinal implant may include processing circuitry. The processing circuitry may be configured to receive image data corresponding to a camera field of view, determine whether a particular object is detected within the camera field of view, perform image data processing to enable a representation of a portion of the image data corresponding to an implant field of view to be provided on a retinal implant where the implant field of view is smaller than the camera field of view, and, responsive to the particular object being located outside the implant field
(Continued)

of view, provide a directional indicator in the implant field of view to indicate a location of the particular object relative to the implant field of view.

18 Claims, 25 Drawing Sheets

(51) Int. Cl.
    *G06F 1/16*     (2006.01)
    *G06T 7/11*     (2017.01)
    *G06F 3/01*     (2006.01)
    *G06F 3/03*     (2006.01)
    *A61N 1/36*     (2006.01)

(52) U.S. Cl.
    CPC .............. *G06F 3/011* (2013.01); *G06F 3/013* (2013.01); *G06F 3/0304* (2013.01); *G06K 9/00624* (2013.01); *G06T 5/40* (2013.01); *G06T 7/11* (2017.01); *G06T 2207/10004* (2013.01); *G06T 2207/30201* (2013.01)

(56) References Cited

U.S. PATENT DOCUMENTS

| | | | |
|---|---|---|---|
| 2007/0010757 A1* | 1/2007 | Goodall | A61B 5/04001 600/546 |
| 2013/0035742 A1* | 2/2013 | Talbot | G06K 9/00228 607/54 |
| 2017/0017831 A1* | 1/2017 | Rollend | G06K 9/00228 |
| 2017/0087023 A1* | 3/2017 | Peli | A61F 9/08 |

OTHER PUBLICATIONS

Parih et al., "Performance of visually guided tasks using simulated prosthetic vision and saliency-based cues", Journal of Neural Engineering, vol. 10, No. 2, Published Feb. 28, 2013, Available online at: http://iopscience.iop.org/article/10.1088/1741-2560/10/2/026017/meta.*

* cited by examiner

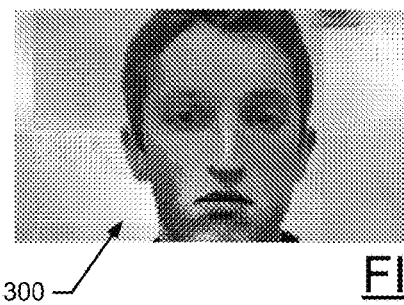
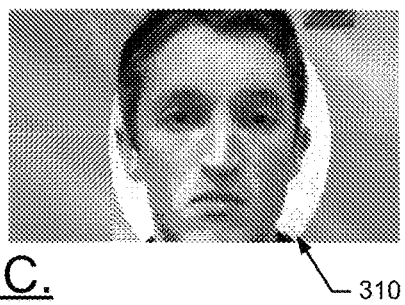
300 — FIG. 4C. — 310
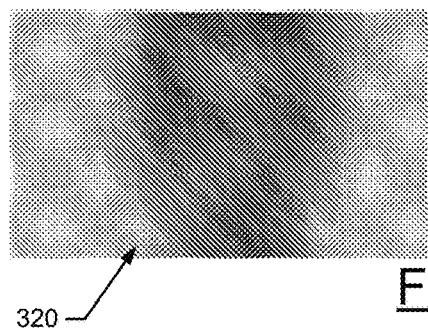
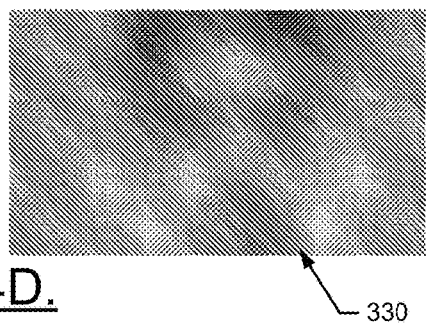
320 — FIG. 4D. — 330
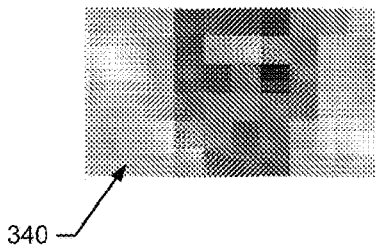
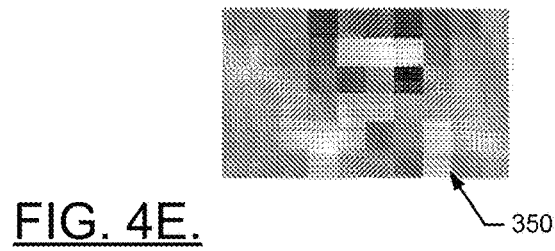
340 — FIG. 4E. — 350

FACE DETECTION, AUGMENTATION, SPATIAL CUEING AND CLUTTER REDUCTION FOR THE VISUALLY IMPAIRED

CROSS-REFERENCE TO RELATED APPLICATIONS

This application claims the benefit of U.S. Provisional Application No. 62/308,204, which was filed on Mar. 14, 2016, and U.S. Provisional Application No. 62/191,780, which was filed on Jul. 13, 2015, the entire contents of each which are hereby incorporated herein by reference.

TECHNICAL FIELD

Exemplary embodiments of the present disclosure generally relate to face detection and clutter reduction technology, and more specifically relate to a system and corresponding hardware for providing face detection various augmentations thereto in the context of a retinal implant.

BACKGROUND

The ability for humans to visually sense features within the environment is a fundamental capability that enables effortless interaction with everyday objects. Too frequently, individuals find themselves with limited or severely impaired vision due to degenerative disorders, trauma, or other diseases. This can make mobility and interaction with objects an arduous task. Several commercial systems have been developed over the last several decades that provide at least a subset of the patient population with the ability to perceive information about the environment. One such system is the ARGUS® II retinal prosthesis developed by Second Sight Medical Products (SSMP). The ARGUS® II is an FDA-approved medical device that consists of wearable glasses (with an integrated monocular camera), a 60-channel (10×6) electrode array and a video processing unit (VPU) used to host computer vision algorithms that ultimately determine which electrodes to stimulate and the intensity of that stimulation. One of the major challenges of the system is to distill the numerous and varying visual features represented in a typical world scene down to a 60-channel electrode array. This problem becomes exacerbated when trying to locate an object or a face, particularly in the presence of clutter.

BRIEF SUMMARY OF SOME EXAMPLES

Some example embodiments may enable the provision of a system for providing a means to reduce background clutter, thereby highlighting objects of interest to the blind individual. Some example embodiments may also provide a description of optimization strategies that may enable clutter reduction algorithms to run on an embedded platform in real-time high speeds (e.g., at 30 frames per second (fps)). Some examples may also provide an image processing pipeline that allows for object and face localization in cluttered environments as well as various contrast enhancement strategies in an implanted image. Some example embodiments may also provide a method for providing spatial cueing. Moreover, some example embodiments may enable sighted persons to experience having a retinal implant to provide better opportunities for testing simulate images seen using a retinal implant so that development can be enhanced. Example embodiments may provide a real time implementation and deployment of the system on a visual prosthesis platform so that advances can significantly improve the effectiveness of the next generation of retinal prosthesis (or implant).

In one example embodiment, an apparatus for improving performance of a retinal implant is provided. The apparatus may include processing circuitry that may be configured to receive image data corresponding to a camera field of view, determine whether a particular object is detected within the camera field of view, and perform image data processing to enable a representation of a portion of the image data corresponding to an implant field of view to be provided on a retinal implant where the implant field of view is smaller than the camera field of view. The processing circuitry may be further configured to, responsive to the particular object being located outside the implant field of view, provide a directional indicator in the implant field of view to indicate a location of the particular object relative to the implant field of view.

In another example embodiment, a method for improving performance of a retinal implant may be provided. The method may include receiving image data corresponding to a camera field of view, and determining whether a particular object is detected within the camera field of view. The method may further include performing image data processing to enable a representation of a portion of the image data corresponding to an implant field of view to be provided on a retinal implant where the implant field of view is smaller than the camera field of view, and, responsive to the particular object being located outside the implant field of view, providing a directional indicator in the implant field of view to indicate a location of the particular object relative to the implant field of view.

BRIEF DESCRIPTION OF THE SEVERAL VIEWS OF THE DRAWING(S)

Having thus described example embodiments of the invention in general terms, reference will now be made to the accompanying drawings, which are not necessarily drawn to scale, and wherein:

FIG. 4C shows enhanced and non-enhanced images for an area of an implant field of view in accordance with an example embodiment;

FIG. 4D shows the simulated electrode values correspond to the images of FIG. 4C in accordance with an example embodiment;

FIG. 4E shows raw electrode values correspond to the images of FIG. 4C in accordance with an example embodiment;

Figure 16:
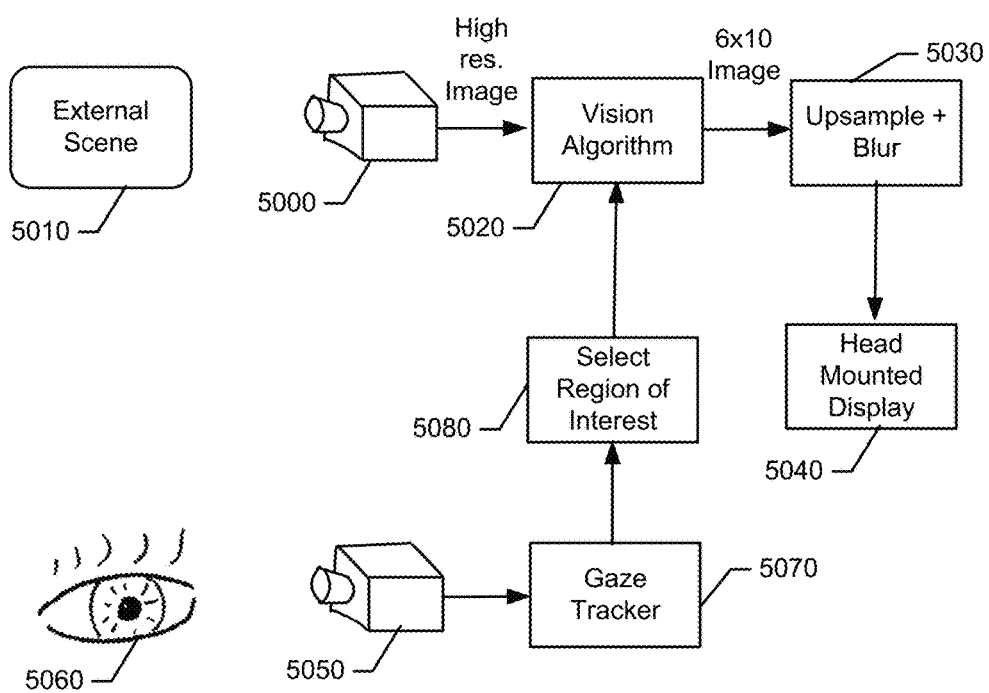
Figure 17:
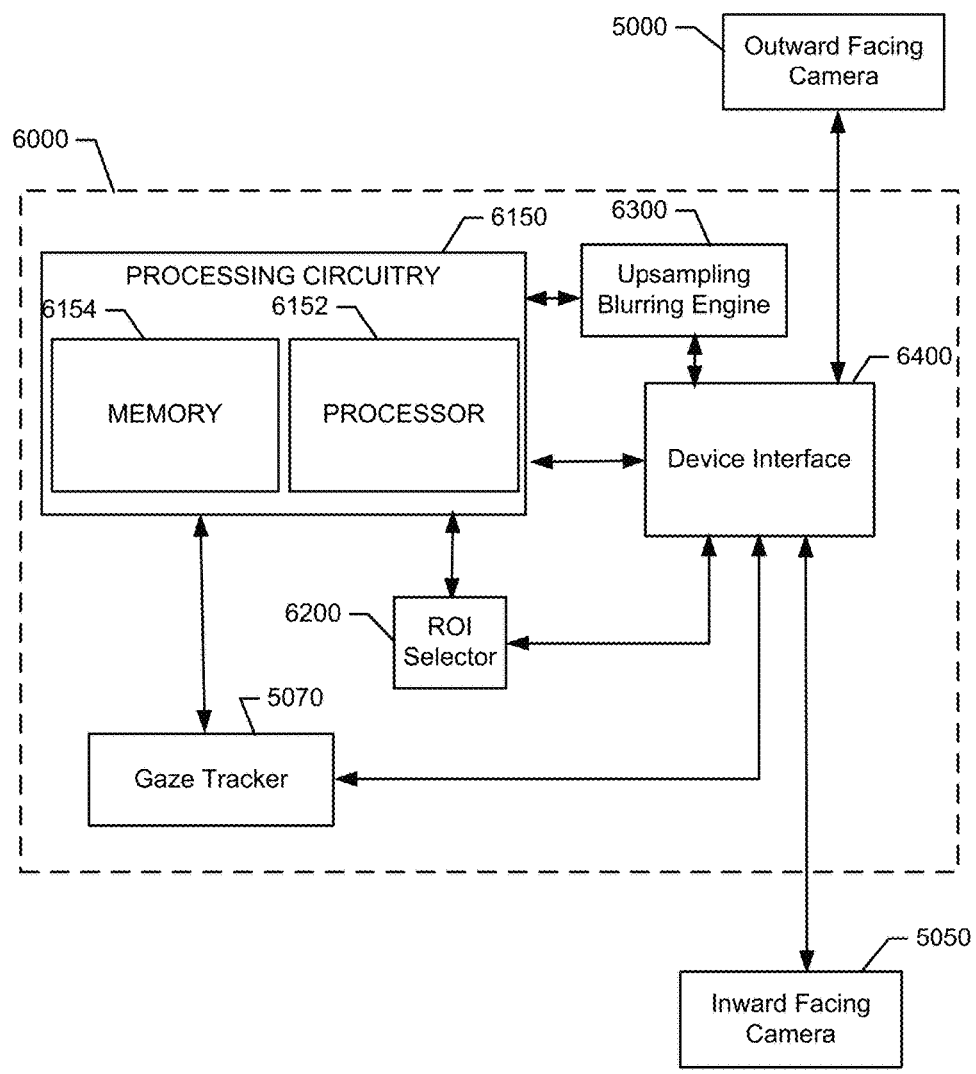
Figure 18:
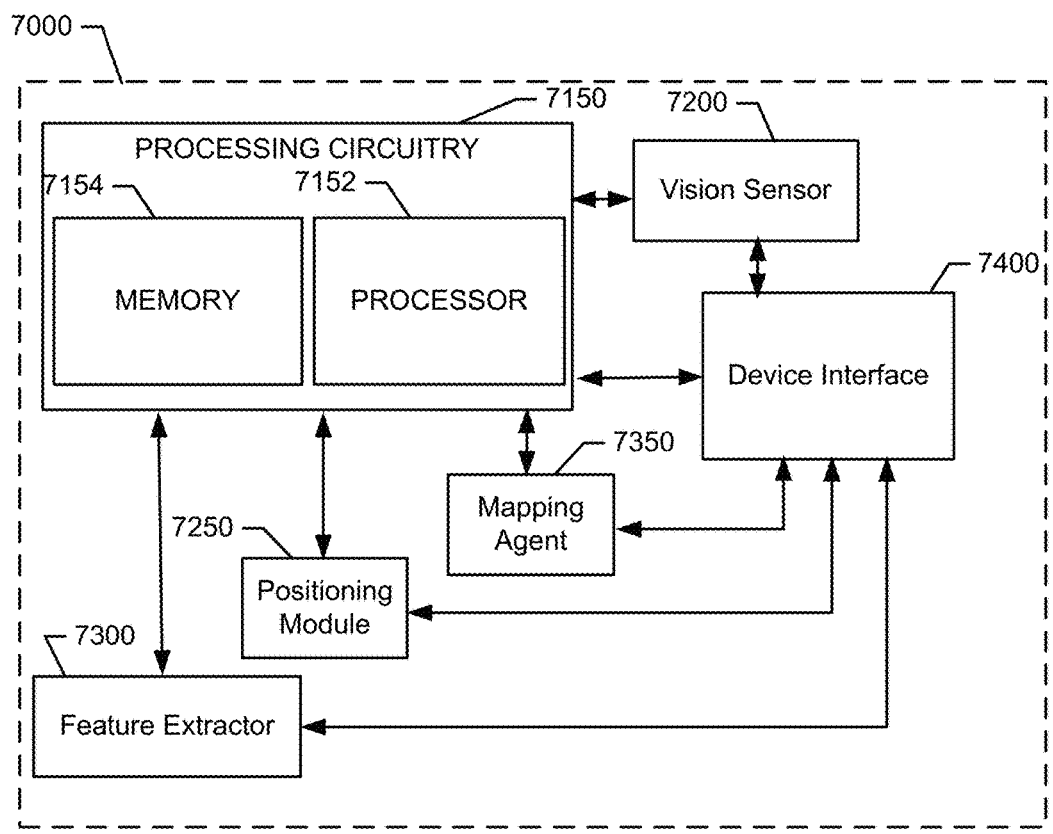

FIG. 16 is a block diagram of a development tool for simulating a retinal prosthesis in accordance with an example embodiment; and FIG. 17 illustrates a block diagram showing components of an apparatus used for providing the tool of FIG. 16 in accordance with an example embodiment; and FIG. 18 illustrates a block diagram of a tool for visual simultaneous localization and mapping in accordance with an example embodiment.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, operable coupling should be understood to relate to direct or indirect connection that, in either case, enables functional interconnection of components that are operably coupled to each other.

Example embodiments may provide a system that can process input images to improve face detection and/or to provide improved clutter reduction. As such, in some cases, example embodiments may provide corresponding sets of algorithms or processing techniques for respective different environments, situations or tasks. In cases where the wearer of the visual prosthesis is viewing a face or a specific object, the system may provide face (or object) detection algorithms that can enhance face detection and/or provide spatial cueing to enable the wearer to be aware of how to move the camera so that the detected face (or object) also moves toward the center of the field of view (FOV) of the retinal implant. In cases where the wearer of the visual prosthesis is viewing an object or environment where clutter may be present, the system may provide techniques for reducing the clutter or the effects of the clutter. Some example embodiments may enable a wearer to shift between modes (e.g., a clutter reduction mode and a face detection mode), or such mode shifts may be handled automatically or semi-automatically. Some example embodiments may also provide a system for enabling sighted individuals to experience the view of a wearer of a visual prosthesis to allow easier testing and evaluation of algorithms and vision processing techniques for the visual prosthesis.

Some example embodiments are therefore directed to an improved spatial fitting and training system for a visual prosthesis. The disclosed system maps projected locations of percepts, where a person perceives a percept from a visual prosthesis to the intended location of the percepts. The projected location may vary over time. The test results can be used to correct a visual prosthesis or spatially map the visual prosthesis.

Figure 1A:
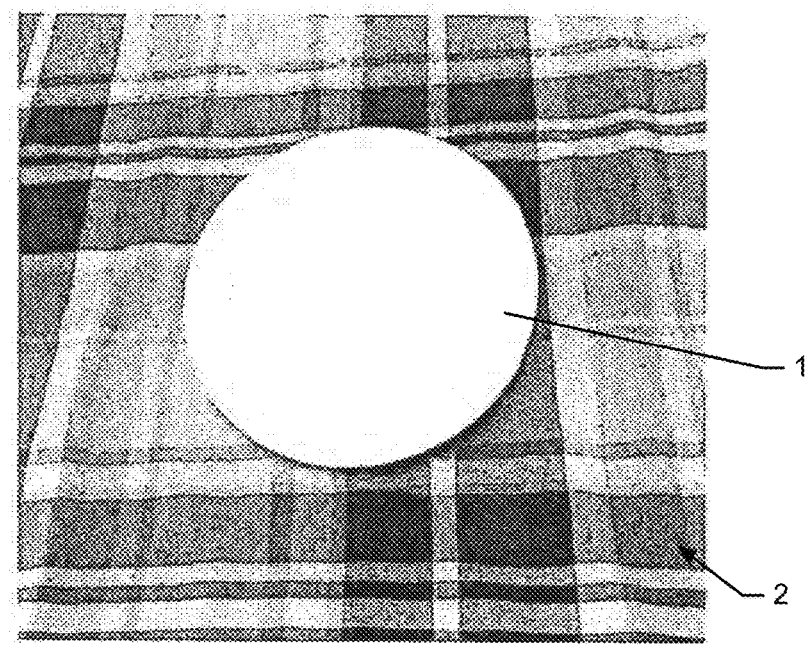
FIG. 1A illustrates an object on a cluttered background that may be captured by a camera.
Figure 1B:
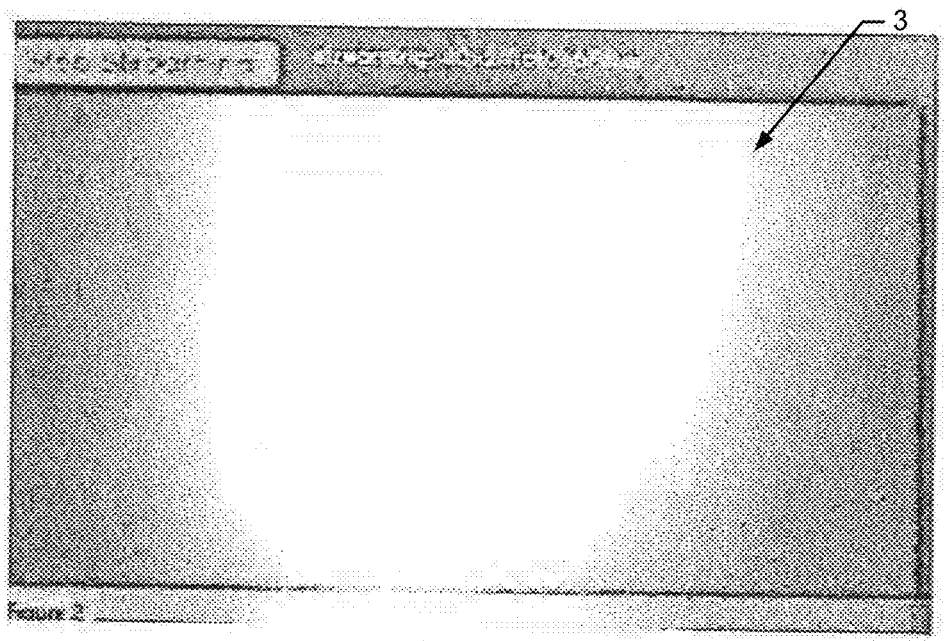
FIG. 1B illustrates how the object may appear when a mean shift algorithm is applied to the object of FIG. 1A in accordance with an example embodiment.

One of the main challenges identified by patients using the ARGUS® II system is the difficulty in finding objects in cluttered backgrounds. In this regard, FIG. 1A shows a generic object 1, in a cluttered background 2. FIG. 1B illustrates an image processing result 3 associated with presentation of the object 1 on an electrode array using legacy techniques. In this example, the complex textured pattern, which forms the cluttered background 2 in the table cloth, generates artifacts in the electrode array making it difficult to locate the object 1 on the table. Similar behavior can also be demonstrated in certain lighting conditions where a gradient in the image intensity is perceived as artifacts in the image.

Thus, one desirable application of example embodiments is to address object localization in cluttered backgrounds. Example embodiments may employ either of two clustering algorithms, K-Means and Mean Shift algorithms, to improve object localization in cluttered backgrounds. These algorithms may enable a visual scene to be represented by relatively few regions of uniform intensity that correspond to the dominant colors in the scene. As a result, texture and other high frequency spatial information can be removed from the scene except at the cluster boundaries, thereby making it easier to perceive large features in the scene.

The K-Means and Mean Shift algorithms are complementary in terms of their advantages and disadvantages. K-Means is a procedure for partitioning a set of data into k clusters. The algorithm works by iterating two key steps: First, each data point is assigned to the cluster with the nearest mean, and then each cluster mean is recomputed as the centroid of the data belonging to that cluster. The algorithm terminates when the cluster assignments stop changing. Efficiency is a primary advantage of K-Means, with drawbacks being that the number of clusters must be known in advance and the algorithm is sensitive to initialization of the cluster means.

Mean Shift is a procedure founded on kernel density estimation for locating the primary modes of a density function given a set of observed data drawn from that function. Mean Shift works by first defining a kernel function around an element of data and computing the kernel-weighted mean of the surrounding data; next, the data point is repositioned at this computed mean. This process iterates until the computed mean stops moving and is performed independently for each element of data. The primary drawback of Mean Shift is its computational complexity, while its advantages include no assumptions made on the number or shape of the clusters and insensitivity to initialization. Classical Mean Shift has one parameter, namely the kernel function bandwidth, which can have a large impact on the clustering outcome. For image based clustering, two bandwidth parameters are used: one for spatial radius and another for the color radius. In some examples employing an embedded implementation, the spatial radius may be limited by computational resources, whereas the color radius may have less impact on runtime and may be more so tuned for optimal clustering performance.

Following clustering by either algorithm, a contrast enhancement stage may be used to make the output clusters more visually distinct for the user. Two types of contrast enhancement have been implemented. The first type is a global enhancement that increases the difference between the min and max cluster intensities by a fixed magnitude (adjusting the min and max value each by half of this magnitude). This is done by linearly stretching the spread of the cluster intensities to match the new min/max range and then shifting the resulting set of intensities as needed to maintain a valid intensity output.

The second type of contrast enhancement is a local enhancement that enforces a minimum contrast between any two clusters. Starting from the cluster of lowest intensity, the intensities of other clusters are increased as needed to obtain the minimum cluster separation; comparison then moves to the cluster of next higher intensity until all cluster pairs have been examined. This method is currently only used for K-Means, since Mean Shift does not explicitly represent its output as a discrete set of clusters. However, the second method could be implemented for Mean Shift by using post-processing to detect the number of output clusters and the cluster associations.

Clustering by K-Means is performed within the Lab color space, which uses dimension L for lightness and dimensions a and b for opposing color. The Lab color space is used in order to limit the influence of brightness gradients on the clustering outcome. This may be accomplished by multiplying the L dimension by some factor less than 1, thereby placing greater emphasis on pixel color. For clustering by Mean Shift, the standard RGB color space may be used.

Figure 2:
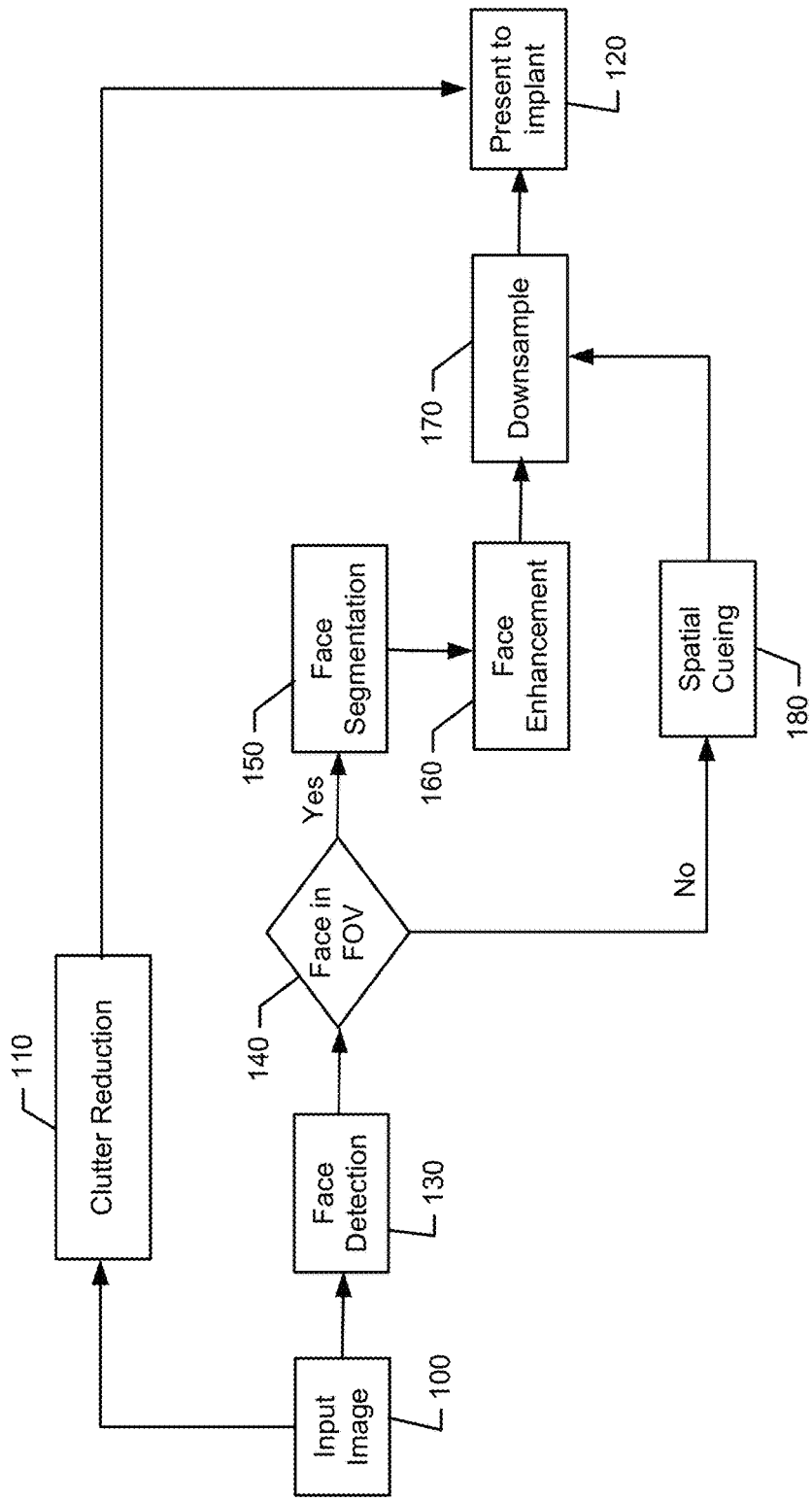
FIG. 2 illustrates a block diagram of a series of operations performed by an image processing system in accordance with an example embodiment.

As mentioned above, another feature often requested by blind individuals is to select a mode where only faces in the scene are highlighted by the retinal implant. This allows the patient to clearly identify and recognize people in a room without having to rely on audio cues. Thus, a system according to an example embodiment may be configured to employ a face (or object) detection mode and a clutter reduction mode. FIG. 2 illustrates a block diagram of a process flow for employing multi-mode input image processing for face detection or clutter reduction in accordance with an example embodiment. In this regard, FIG. 2 shows a series of processing steps that can be used in a manner that eliminates or mitigates many of the issues discussed above.

The processes of FIG. 2 may be performed within the context of a system configured to perform video processing on images captured via glasses or other optical equipment (e.g., a camera) that is forward looking and is operably coupled to a retinal prosthesis. The optical equipment has a FOV that is larger than the FOV of the retinal prosthesis, which employs an electrode array of limited size (e.g., 10×6). Example embodiments may enable video processing techniques to be employed to reduce clutter or improve face detection, as mentioned above. In this regard, the face detection may be provided relative to the FOV of the camera to find faces within image data gathered by the camera. The face region may be enhanced, and the background region may be diminished when the face region is within the FOV of the retinal implant. However, if the face region is not within the FOV of the retinal implant, then visual cues may be provided to the subject or patient to indicate where the face is located within the camera frame (i.e., within the FOV of the camera) in order to allow the subject to move his/her head to move the face region into the FOV of the retinal implant. These visual cues are provided as spatial cueing.

As shown in FIG. 2, an input image 100 may be received and then, dependent upon the mode of operation of the system, the input image 100 may either be processed for clutter reduction with a selected clutter reduction algorithm 110 before presentation to the implant 120, or the input image 100 may be processed for face detection with a selected face detection algorithm 130. The face detection algorithm 130 may include an initial operation of determining whether a face is located within the FOV of the implant at operation 140. If the face is located within the FOV of the implant, then face segmentation 150 may be performed prior to the performance of face enhancement 160. Downsampling may then be performed at operation 170 prior to presentation to the implant 120. In the face is not located in the FOV of the implant, then spatial cueing 180 may be performed prior to downsampling at operation 170 and presentation to the implant 120.

In some cases, the face detection algorithm 130 may use the classical Viola-Jones cascaded classifier detection method available in OpenCV, operating on local binary pattern (LBP) features. When a face is first detected using LBP features, a second cascaded classifier based on Haar features may be used to verify the face and reduce false positives. Despite the fact that LBP features are generally considered to be very efficient, the face detection portion is the most computationally expensive part of the entire face detection module and is therefore a ripe area for various optimizations.

Figure 3A:
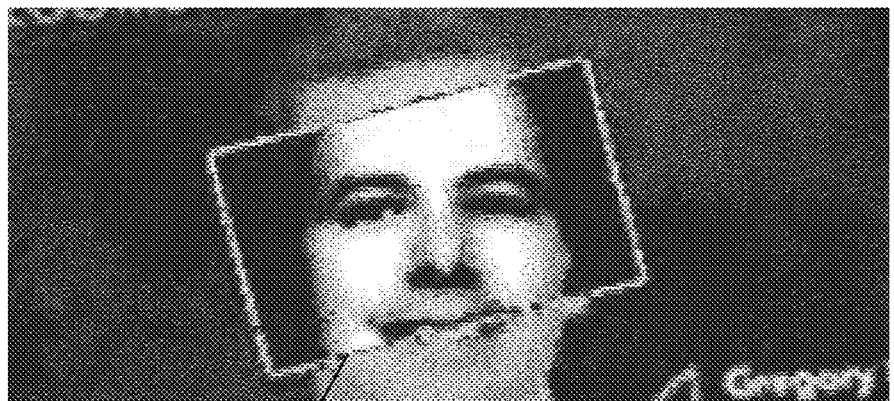
FIG. 3A illustrates a sample output of a face enhancement algorithm in accordance with an example embodiment.
Figure 3B:
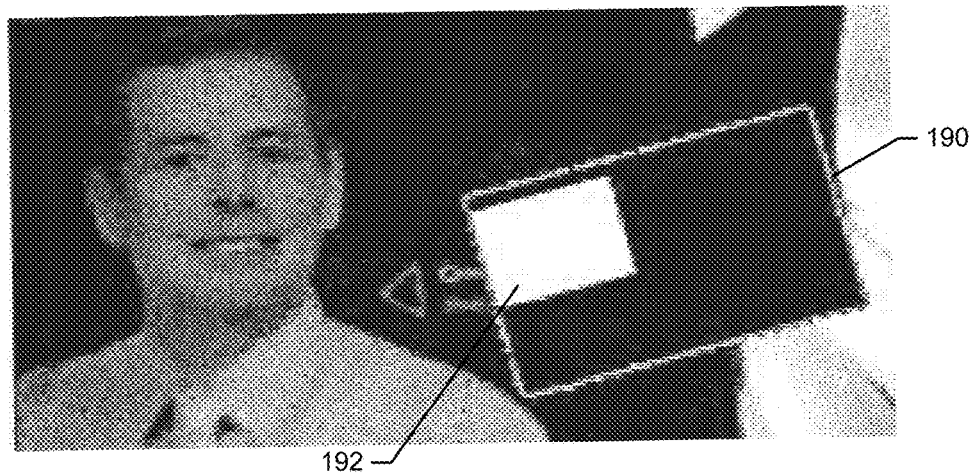
FIG. 3B illustrates a sample output involving spatial cueing in accordance with an example embodiment.

When a detected face intersects the implant FOV 190, an oval or elliptical region around the face may be segmented, contrast enhanced via histogram equalization, intensity, contrast, or other adjustments, and then added back to the reduced intensity background region around the face, as shown in FIG. 3A (note that the output shown does not include the downsampling to the required 10×6 electrode input). Spatial cueing may be used when a detected face lies outside the implant FOV to indicate to the user where the face is relative to where they are currently looking. The concept of spatial cueing is illustrated in FIG. 3B wherein a bright stimulation rectangle 192 is presented on the edge of the electrode array closest to where the face is present in the global forward-facing camera FOV. When a certain amount of intersection between the detected face and the implant FOV 190 region occurs as the user moves their head towards the face, the algorithm will switch to face enhancement 160 in FIG. 2 above. This process is further illustrated in some specific examples shown in FIGS. 4A to 4H. In some example embodiments, optimization strategies may be performed to allow the algorithms described herein to run in real-time at 30 fps on a processor or processing circuitry configured to execute the algorithms.

Figure 4A:
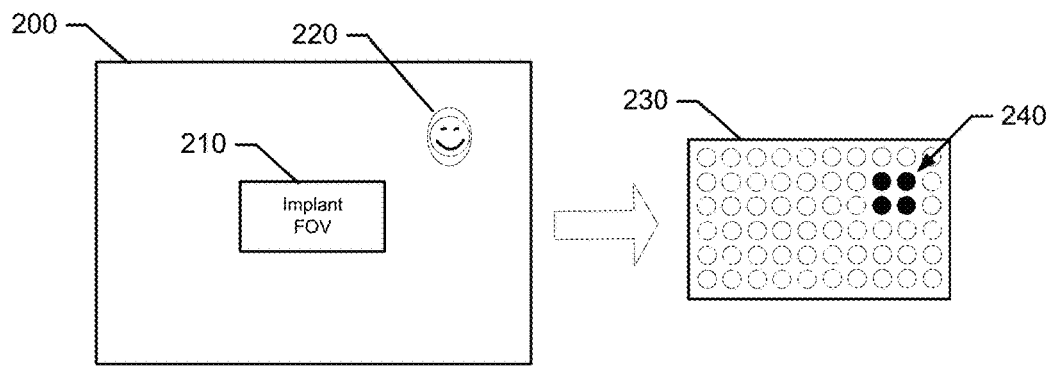
FIG. 4A illustrates a wide field of view type of spatial cueing in accordance with an example embodiment.
Figure 4B:
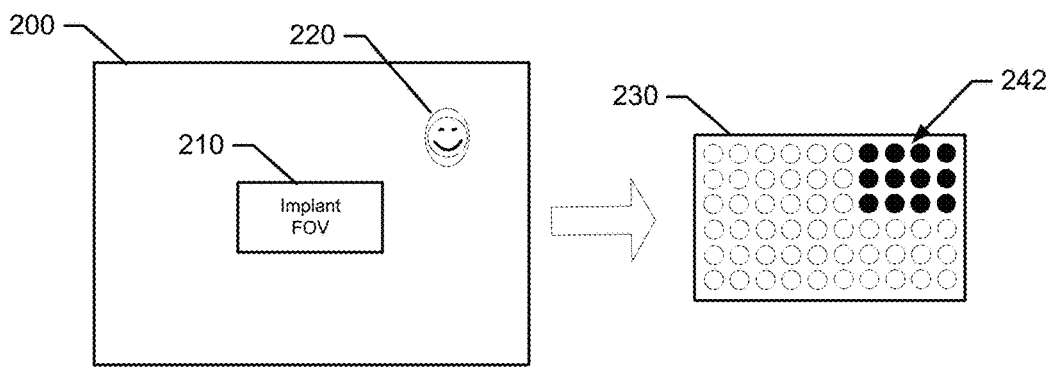
FIG. 4B illustrates a normal field of view type of spatial cueing in accordance with an example embodiment.

FIG. 4A illustrates first example of spatial cueing according to an example embodiment, and FIG. 4B illustrates a second example. As shown in FIGS. 4A and 4B, a camera FOV 200, which may be about 320×240 pixels in some cases, may detect image data therein corresponding to a series of camera frames. Meanwhile, the implant FOV 210 is much smaller (e.g., 160×96 pixels nominal). When, as mentioned above, a face region 220 is detected outside the implant FOV 210, spatial cueing may be performed. The spatial cueing can be provided in a number of different ways, and FIGS. 4A and 4B illustrate specific examples of wide FOV and narrow FOV spatial cueing.

In this regard, FIG. 4A shows an electrode array 230 having a directional indicator 240 provided thereon according to a wide FOV example. The directional indicator 240 acts as a spatial cue to indicate the direction relative to the implant FOV 210 where the face region 220 can be located. The directional indicator 240 of this example has an indication paradigm that provides a demonstration of the location of the face region 220 relative to the entire FOV (i.e., the camera FOV 200). In other words, the camera FOV 200 is mapped to the electrode array 230 with an indication of where the face region 220 is relative to the camera FOV 200. Thus, the directional indicator 240 in this example activates selected electrodes to indicate that the face region 220 is relatively close to the top right hand corner of the camera FOV 200. The user or subject then knows to focus slightly right and upward if it is desirable to move the face region 220 into the implant FOV 210. The size of the directional indicator 240 may be selected at any desirable number of electrodes. Moreover, the size of the directional indicator 240 could be selected to be different than that of any other modes so that characteristics (e.g., size, shape, intensity, blink pattern/frequency, display pattern, etc.) of the directional indicator 240 further indicate the type of spatial cue being provided (e.g., wide FOV or normal FOV spatial cueing).

In the example of FIG. 4B, normal FOV cueing is demonstrated via a different directional indicator 242. In normal FOV cueing, the electrodes may be activated in a pattern that indicates the type of spatial cute being provided based again on characteristics of the electrode activation used to generate the directional indicator 242. Normal FOV cueing may indicate the direction outside the implant FOV 210 at which the face region 220 can be found in the camera FOV 200. Thus, in this example, the upper right corner of the electrode array 230 may be activated to indicate that the face region 220 is located up and to the right relative to the implant FOV 210.

Accordingly, example embodiments may provide directional indicators having characteristics that indicate the type of directional indication provided thereby, and that indicate to the user or subject how to bring the face region 220 into the implant FOV 210 when the face region 220 is outside the implant FOV 210. The directional indicators may be presented constantly or as pulsing intensity indicators, and may be provided independent of downsampled images or, in some cases, may be provided as an overlay on top of downsampled images presented to the electrode array. This can be helpful in enabling the subject or patient to bring an object or face into the implant FOV 210. However, it is also worth considering that the subject or patient may benefit from keeping the object or face in the implant FOV 210 even after it has moved out of the implant FOV 210 under some circumstances. For example, in some cases, an object/face or the direction of the gaze of the subject or patient may change rapidly for a brief time for some reason. If the face representation that was presented in the implant FOV 210 is cycled between being presented and being replaced with directional indicators, the subject may become disoriented. Thus, in some cases, the face may continue to be presented (e.g., as a ghost image) for a predetermined period of time after the face is no longer in the implant FOV 210. Similarly, for example, when a face is no longer detected because it has exited the camera frame entirely, a ghost image of the previous output (including the prior directional indicator) may be provided for a predetermined period of time or number of frames. Accordingly, presentations may be stabilized over time to provide improved consistency and stability of presentation and avoid hysteresis.

While facial cueing methods may assist the subject in localizing a detected face within the camera FOV 200, it may be further desirable to enhance the appearance of the face when displaying the face within the implant FOV 210. Some example embodiments may therefore employ enhancement filters or other enhancement techniques when the face region 220 enters or otherwise is in the implant FOV 210. The goal of such filters or techniques is to qualitatively enhance the face region of the input image and decrease the amount of background information presented to the user. Doing so may afford easier focusing for patients in order to increase interpersonal communication abilities.

FIG. 4C illustrates a non-enhanced implant FOV image 300 and a corresponding enhanced implant FOV image 310. The enhanced implant FOV image 310 may initially have an ellipse formed around the face to define a region of interest (ROI). Enhancements of various types may be performed on the ROI, while the background is not enhanced. In some cases, intensity, contrast, or other adjustments may be performed within (or outside) the ROI. Cropping and rotation of images may also be provided in connection with filtering. In this regard, the implant FOV 210 may be rotated and/or cropped by the application of rotation angles and/or offset parameters. FIG. 4D illustrates simulated 10×6 electrode values for an unenhanced case 320 and an enhanced case 330. FIG. 4E illustrates raw 10×6 electrode values for the corresponding unenhanced case 340 and enhanced case 350.

Figure 4F:
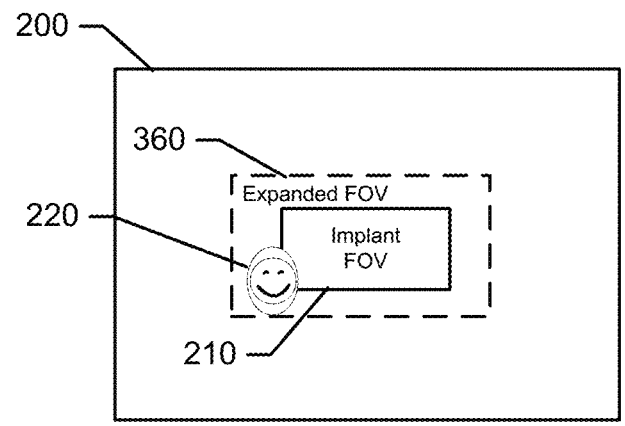
FIG. 4F illustrates an expanded field of view employed to detect faces in accordance with an example embodiment.
Figure 4G:
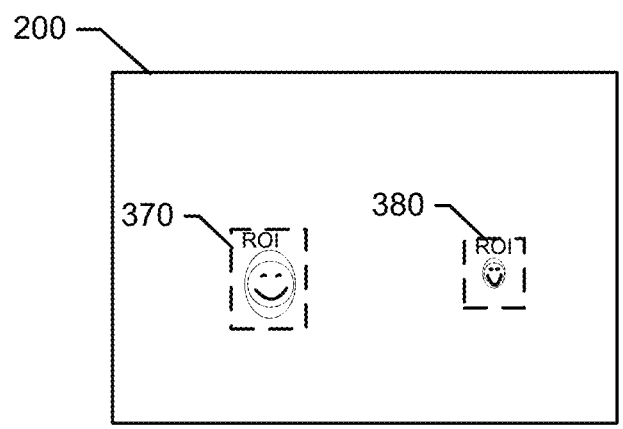
FIG. 4G illustrates different sizes of regions of interest in accordance with an example embodiment.

As mentioned above, face detection may be employed with, for example, LBP or Haar based cascade. There are two primary factors that determine the execution time of the cascaded classifier used in the face detection algorithm: the input image resolution and the required detectable face size. A single pyramidal down sample may be performed to reduce the input image resolution from 640×480 to 320×240 before face detection. To further reduce the amount of data to be processed, only an expanded implant FOV region 360 may be considered during initial detection as shown in FIG. 4F. The amount of expansion may be configurable and may be set based on the maximum detectable face size. After a face has been detected and verified, a tracking phase may be employed. During the tracking phase, detection may only be performed on a slightly expanded ROI 370 around the current face location as shown in FIG. 4G. The size of the ROI may be decreased if the face size is smaller such as for smaller ROI 380. Thus, in both the initial detection and tracking phases, the amount of expansion may be dictated by the detectable face size. The maximum and minimum detectable face sizes may be determined by the camera FOV, face anthropometry, and by the sizes of faces used to train the cascaded classifier.

During initial detection, the implant FOV may be expanded by a configurable fraction of the maximum face size, nominally 30 pixels on all sides of the downsampled FOV size (80×48) for a total operating area of 140×108 pixels. This enables detection down to 0.25 m (_10 inches) from the camera. The minimum face size during initial detection, 24×24 pixels, is determined by the trained cascaded classifier and allows for detection up to 2 m (_6.5 ft) from the camera with some embodiments of the system. Thus, some example embodiments may employ scaling to resize input images using an iterative process in conjunction with the face detection algorithm. Essentially, an image pyramid may be created in which larger faces may be shrunk to fit within the trained detection window size (e.g., 24×24 pixels). A face scale factor of 1.05 may be employed in some embodiments to resize an image that is 5% smaller than a previous image at each stage of detection.

During the tracking phase (after initial face detection and verification), the maximum and minimum face sizes may be set dynamically based on a current bounding box around the face. The maximum size may be based on a small padding added to the current bounding box, nominally one-third of the current width and height. The minimum size may be set to half of the current face bounding box size or the minimum detectable face size parameter, whichever is larger. This adaptive search ROI enables faster than real-time operation after a face has been detected. These optimizations may improve the qualitative user experience as well as to reduce computational strain on the VPU system as a whole. The high latency induced in the non-optimized case makes it difficult for the algorithm to keep pace with the changing input images as users move their head to scan the environment, causing spurious detections and no temporal consistency. Additionally, having the nominal runtime consistently higher than the frame rate (30 frames/s or 33 ms/frame) would drive the system's CPU utilization towards 100%, making it an unrealistic scenario for a real-time embedded system. Table I provides a summary of the effect of the various optimization strategies used in the face detection algorithm.

Optimization Summary for the Face Detection Algorithm

TABLE 1

| Algorithm Phase | Non-optimized (ms) | FOV + ROI (ms) | Speedup |
|---|---|---|---|
| Initial detection | 402.9 | 43.4 | 9.3X |
| Verification | 558.3 | 164.9 | 3.4X |
| Tracking | 402.9 | 18.9 | 21.3X |

Face segmentation may be performed in connection with motion representation during the tracking phase. In some cases, the contours of the face, eyes, mouth and/or other facial features may be enhanced or otherwise modified during face segmentation. Face segmentation may be performed in connection with use of an ellipse (as described above), hue bandpass filtering, or K-means processing on hue.

Face enhancement may be performed by increasing face intensity and decreasing background intensity. Contrast enhancement and blurring of external regions apart from the face may also be performed. Foreground and background filtering techniques may also be employed in addition to, or as an alternative to, altering feature contours.

Figure 4H:
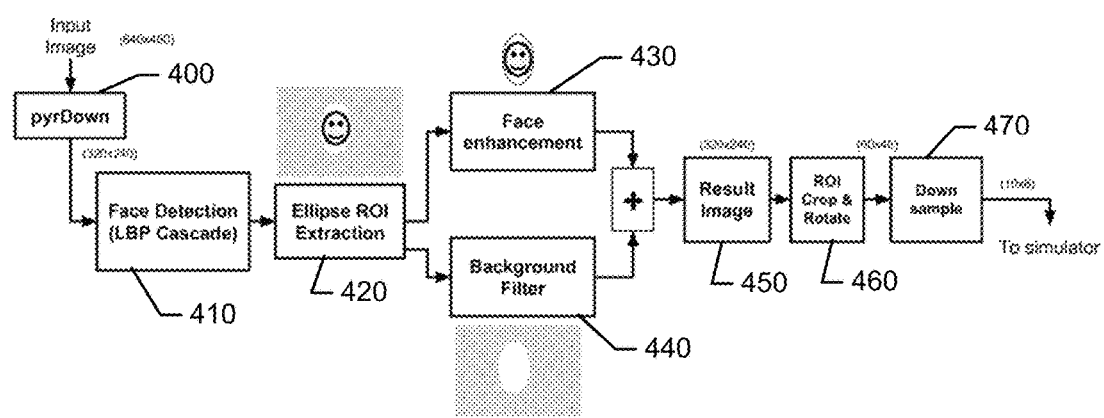
FIG. 4H illustrates a block diagram showing operations associated with face detection and enhancement in accordance with an example embodiment.

FIG. 4H illustrates a block diagram summarizing various ones of the operations discussed above relative to face detection and filtering. In this regard, the input image may initially be reduced in size at operation 400. Then face detection 410 may be conducted to determine the location of faces within a camera image. Ellipse ROI extraction may then be performed at operation 420 to identify a face region. Thereafter, and possibly simultaneously and/or in parallel, face enhancement 430 may be performed while the background is filtered at operation 440. A resulting, size reduced image may be generated at operation 450 prior to ROI cropping and rotation at operation 460. The cropped and/or rotated image may then be downsampled 470 to generate and output for the 10×6 electrode array.

Meanwhile, when no object or face is necessarily within the FOV, clutter reduction may be employed. In an initial implementation of K-means clutter reduction optimization executed on a 320×240 downsampled image had a runtime of 8 s on the first run and approximately 700 ms on subsequent runs (subsequent runs are seeded with the cluster centers identified by the previous run). The initial implementation used OpenCV version 2.4.2. Reducing the input resolution to 160×96 reduced the runtime to 160 ms. Removing an extraneous color space conversion further reduced the runtime to 139 ms. Upgrading from OpenCV version 2.4.2 to 3.0.0.beta reduced the runtime to 96 ms. Modifying the implementation of K-means by replacing the OpenCV row copy operation with a direct data pointer access reduced the runtime to 44 ms.

Further reducing the K-means input resolution to 80×60 reduced the runtime to 25 ms, and upgrading to version 3.0.0 reduced the runtime to 22.5 ms which was the final implementation of the algorithm. The initial implementation of the Mean shift algorithm executed at 13 ms requiring no further optimization for real time performance.

Figure 5A:
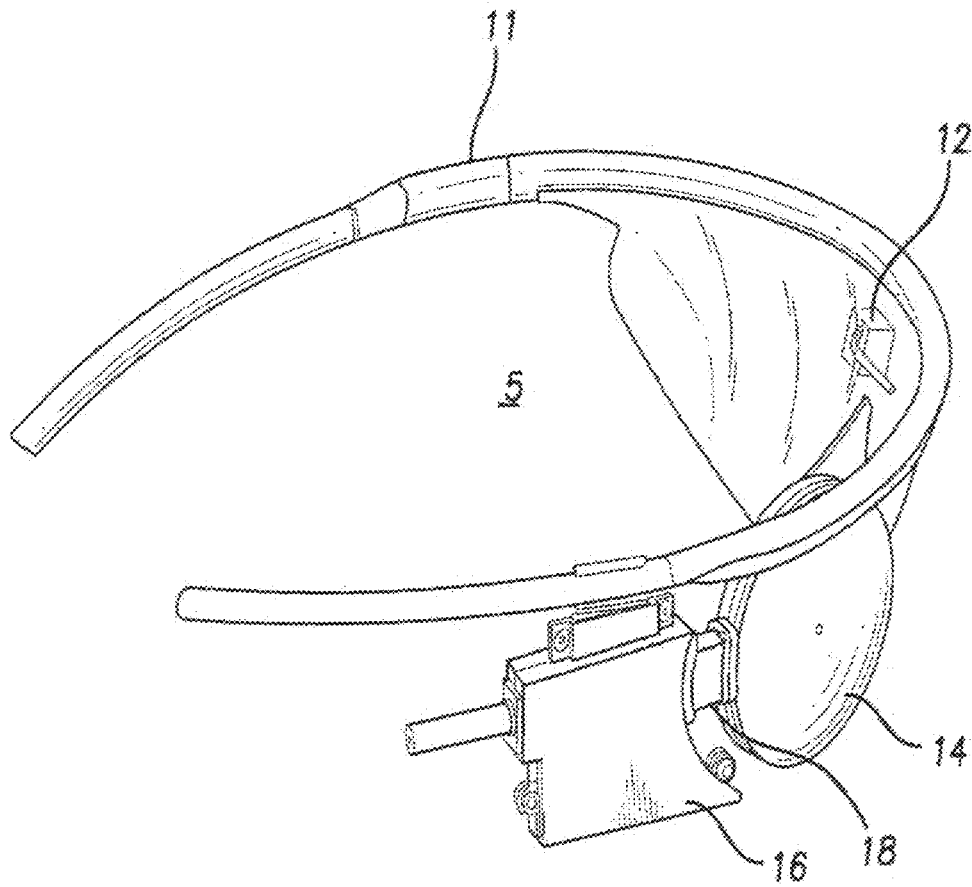
FIGS. 5A and 5B illustrate an example embodiment of an apparatus that may be employed in connection with an example embodiment.
Figure 5B:
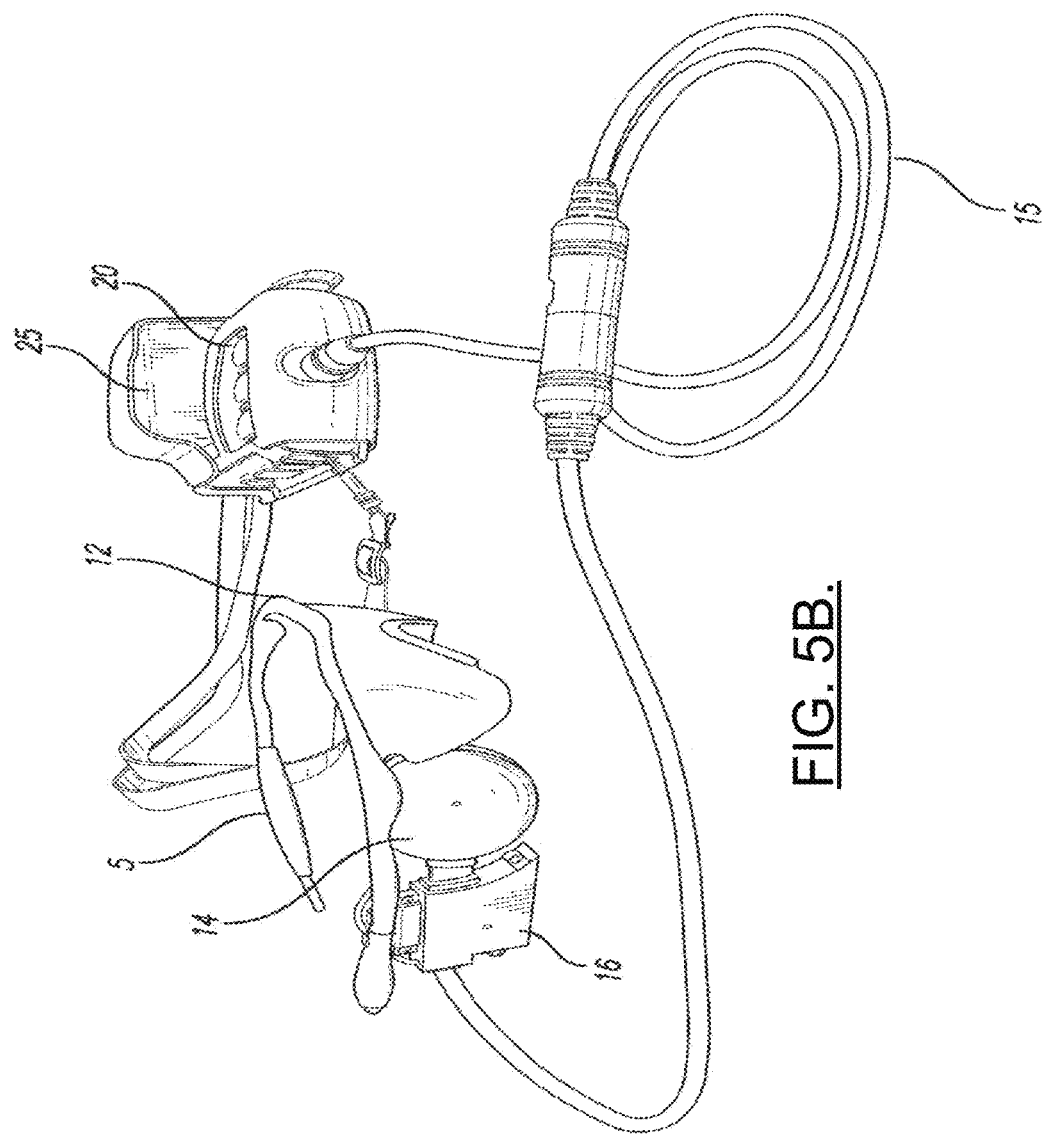

FIGS. 5A and 5B illustrate an example embodiment of an apparatus (e.g., glasses 5) that may be employed in connection with an example embodiment. Referring to FIG. 5, the glasses 5 may include, for example, a frame 11 holding a camera 12, an external coil 14 and a mounting system 16 for the external coil 14. The mounting system 16 may also enclose the RF circuitry. In this configuration, the video camera 12 captures live video as a video signal. The video signal is sent to an external video processing unit (VPU) 20 to which the glasses 5 are operably coupled via a glasses cable 15. The VPU 20 processes images from the video signal relative to a FOV of the camera. The VPU 20 processes the video signal and subsequently transforms the processed video signal into electrical stimulation patterns or data. The electrical stimulation data are then sent to the external coil 14 that sends both data and power via radio-frequency (RF) telemetry to a secondary coil 2016 (see FIG. 11 below) of the retinal stimulation system 2000. The secondary coil 2016 receives the RF commands which control an application specific integrated circuit (ASIC), which in turn delivers stimulation to the retina of the subject via a thin film electrode array (TFEA).

In some example embodiments, light amplitude is recorded by the camera 12. The VPU 20 may use a logarithmic encoding scheme to convert the incoming light amplitudes into the electrical stimulation patterns or data. These electrical stimulation patterns or data may then be passed on to the retinal stimulation system 2000, which results in the retinal cells being stimulated via the electrodes in an electrode array (e.g., flexible circuit electrode array 2010 of FIG. 11). In an example embodiment, the electrical stimulation patterns or data being transmitted by the external coil 14 is binary data. The external coil 14 may contain a receiver and transmitter antennae and a radio-frequency (RF) electronics card for communicating with the secondary coil 2016.

Figure 6:
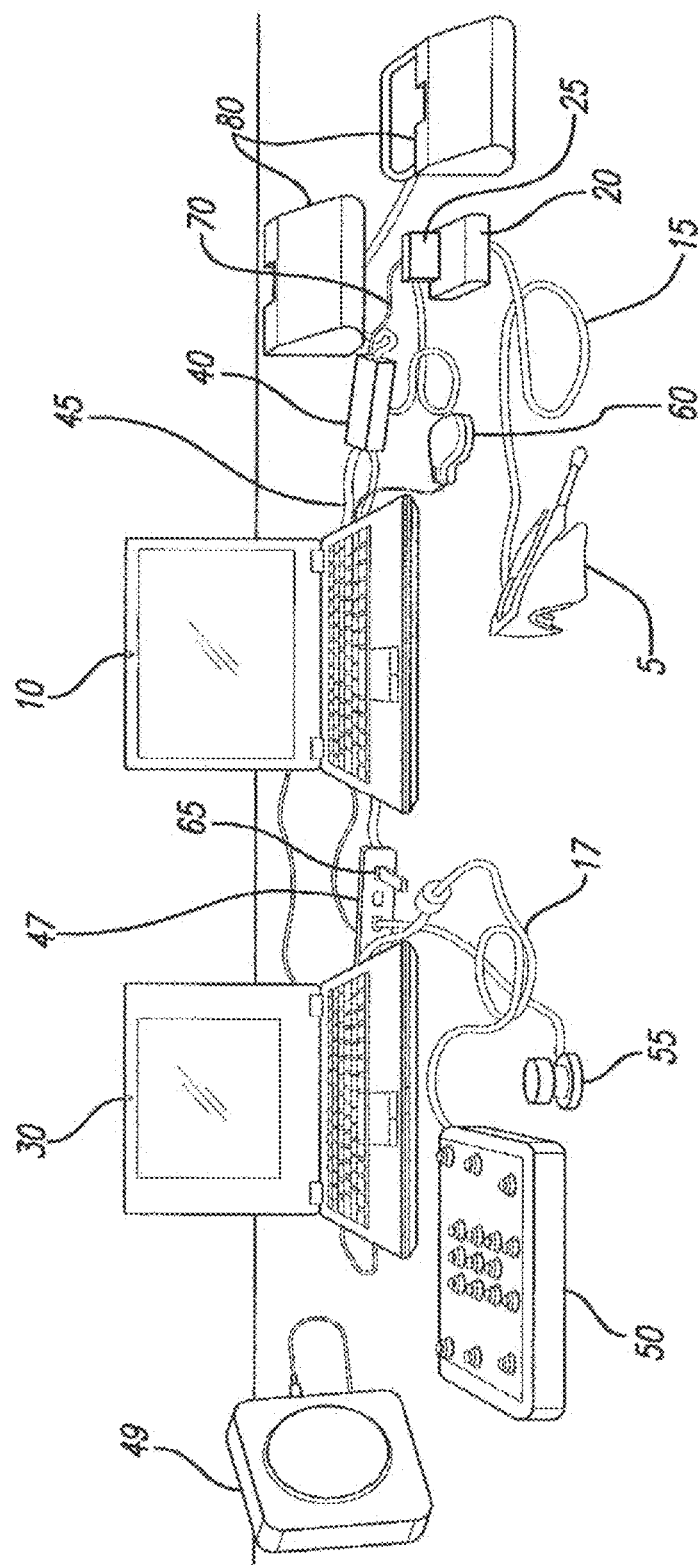
FIG. 6 illustrates a system for processing data associated with the apparatus of FIGS. 5A and 5B in accordance with an example embodiment.
Figure 11:
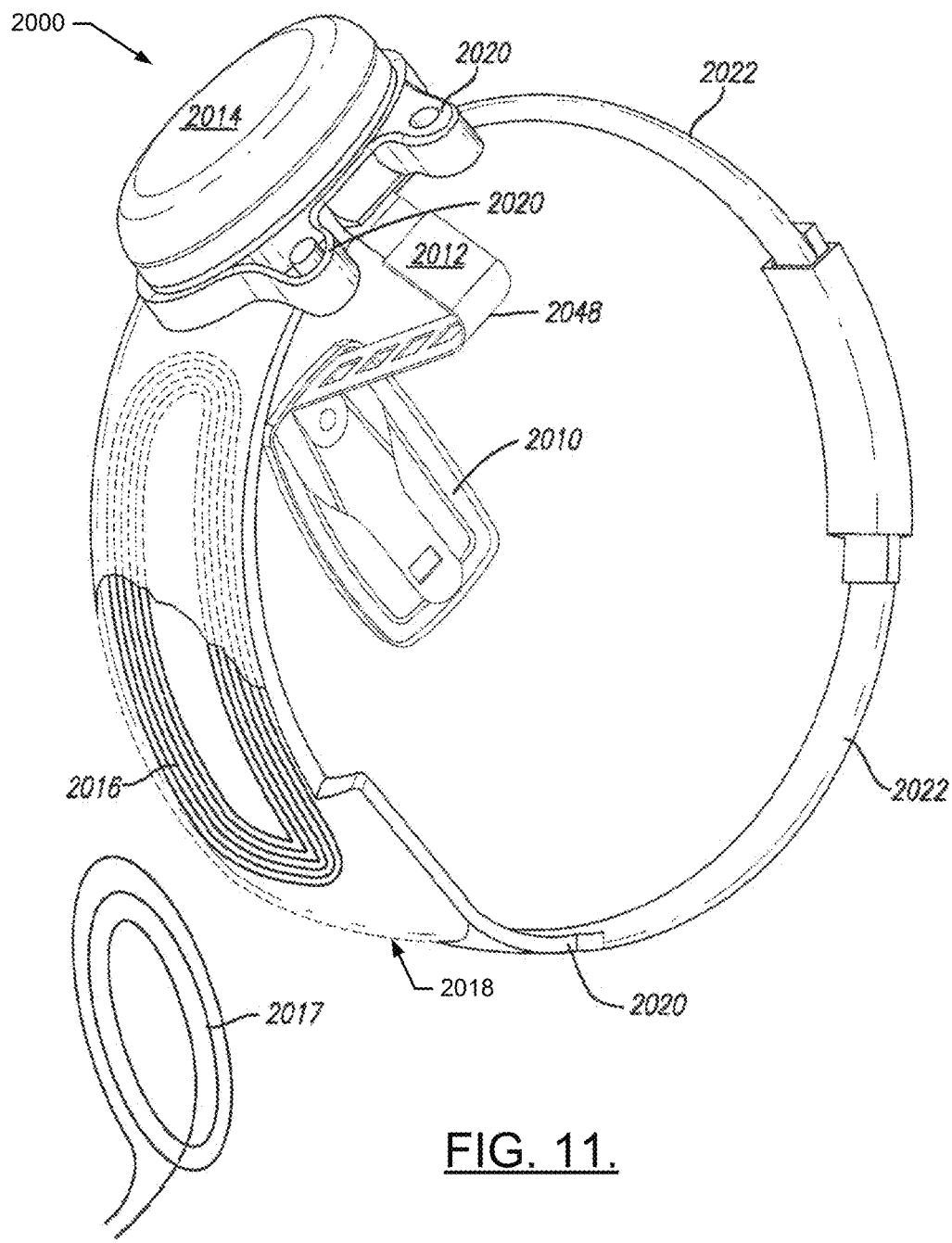
FIG. 11 illustrates a perspective view of an implanted portion of a visual prosthesis in accordance with an example embodiment.

Referring to FIG. 6, a Fitting System (FS) may be used to configure and optimize the visual prosthesis apparatus shown in FIG. 11. The Fitting System is fully described in the U.S. application Ser. No. 11/796,425, filed on Apr. 27, 2007, which is incorporated herein by reference in its entirety.

The Fitting System may include custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the VPU 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the psychophysical test system (PTS), located for example on a dedicated PTS laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB® (MathWorks)™ software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the visual prosthesis or implant for each subject or patient.

The laptop computer 10 of FIG. 6 may be operably coupled to the VPU 20 using an optically isolated serial connection adapter 40. Because it is optically isolated, the serial connection adapter 40 assures that no electric leakage current can flow from the laptop computer 10 in the event of a fault condition.

As shown in FIG. 6, the following components may be used with the Fitting System according to some example embodiments. The VPU 20 for the subject being tested, a charged battery 25 for the VPU 20, the glasses 5, the laptop computer 10, the PTS Laptop 30, a PTS CD (not shown), the connection adapter (CA) 40, a USB drive (Security) (not shown), a USB drive (Transfer) 47, a USB drive (Video Settings) (not shown), a patient input device (RF Tablet) 50, a further patient input device (Jog Dial) 55, glasses cable 15, CA-VPU cable 70, FS-CA cable 45, FS-PTS cable, Four (4) port USB hub 47, mouse 60, test array system 80, archival USB drive 49, an isolation transformer (not shown), adapter cables (not shown), and an external monitor (not shown).

With continued reference to FIG. 6, the external components of the Fitting System may be configured as follows. The battery 25 may be operably coupled to the VPU 20. The PTS laptop 30 is operably coupled to the laptop computer 10 using the FS-PTS Cable. The PTS laptop 30 and laptop computer 10 are plugged into the isolation transformer (not shown) using the adapter cables (not shown). The isolation transformer may be plugged into a wall outlet. The four (4) port USB hub 47 may be operably coupled to the laptop computer 10 at the USB port. The mouse 60 and the two patient input devices 50 and 55 may be operably coupled to four (4) port USB hubs 47. The laptop computer 10 may be operably coupled to the communication adapter (CA) 40 using the FS-CA cable 45. The CA 40 may be operably coupled to the VPU 20 using the CA-VPU Cable 70. The glasses 5 may be operably coupled to the VPU 20 using the glasses cable 15.

In an example embodiment, the Fitting System shown in FIG. 6 may be used to configure system stimulation parameters and video processing strategies for each subject outfitted with the visual prosthesis apparatus of FIGS. 5A and 5B. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the retinal stimulation system 2000. These parameters may be checked to ensure that maximum charge per phase limits, charge balance, and power limitations are met before the test stimuli are presented to the subject. Additionally, these parameters may be checked a second time by the firmware of the VPU 20. The Fitting System shown in FIG. 6 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-temporal electrode stimulation parameters thereby optimizing the effectiveness of the visual prosthesis for each subject.

The visual prosthesis apparatus may operate in two modes: i) stand-alone mode and ii) communication mode. The stand-alone mode is shown in FIG. 5B. In the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system. The internal coil 116 of the retinal stimulation system 1 receives the RF commands from the external coil 14 and transmits them to the electronics package 2014 (see FIG. 11) that in turn delivers stimulation to the retina via the electrode array 2010. Additionally, the retinal stimulation system 2000 may communicate safety and operational status back to the VPU 20 by transmitting RF telemetry from the internal coil (e.g., secondary coil 2016) to the external coil 14. The visual prosthesis apparatus of FIGS. 5A and 5B may be configured to electrically activate the retinal stimulation system 2000 only when it is powered by the VPU 20 through the external coil 14. The stand-alone mode may be used for clinical testing and/or at-home use by the subject.

The communication mode may be used for diagnostic testing, psychophysical testing, patient fitting and downloading of stimulation settings to the VPU 20 before transmitting data from the VPU 20 to the retinal stimulation system 2000 as is done for example in the stand-alone mode described above. Referring to FIG. 6, in the communication mode, the VPU 20 is connected to the laptop computer 10 using cables 70, 45 and the optically isolated serial connection adapter 40. In this mode, laptop computer 10 generated stimuli may be presented to the subject and programming parameters may be adjusted and downloaded to the VPU 20. The PTS laptop 30 connected to the laptop computer 10 may also be utilized to perform more sophisticated testing and analysis in some cases.

In an example embodiment, the functionality of the retinal stimulation system 2000 can also be tested pre-operatively and intra-operatively (i.e. before operation and during operation) by using an external coil 14, without the glasses 5, placed in close proximity to the retinal stimulation system 2000. The external coil 14 may communicate the status of the retinal stimulation system 2000 to the VPU 20 that is connected to the laptop computer 10 of the fitting system as shown in FIG. 6.

As discussed above, the VPU 20 processes the image from the camera 12 and transforms the image into electrical stimulation patterns for the retinal stimulation system. Filters such as edge detection filters may be applied to the electrical stimulation patterns for example by the VPU 20 to generate, for example, a stimulation pattern based on filtered video data that the VPU 20 turns into stimulation data for the retinal stimulation system 2000. The images may then be reduced in resolution using a downscaling filter. In an example embodiment, the resolution of the image may be reduced to match the number of electrodes in the electrode array 2010 of the retinal stimulation system. That is, if the electrode array 2010 has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system in frames that may employ a cyclic redundancy check (CRC) error detection scheme.

Figure 7:
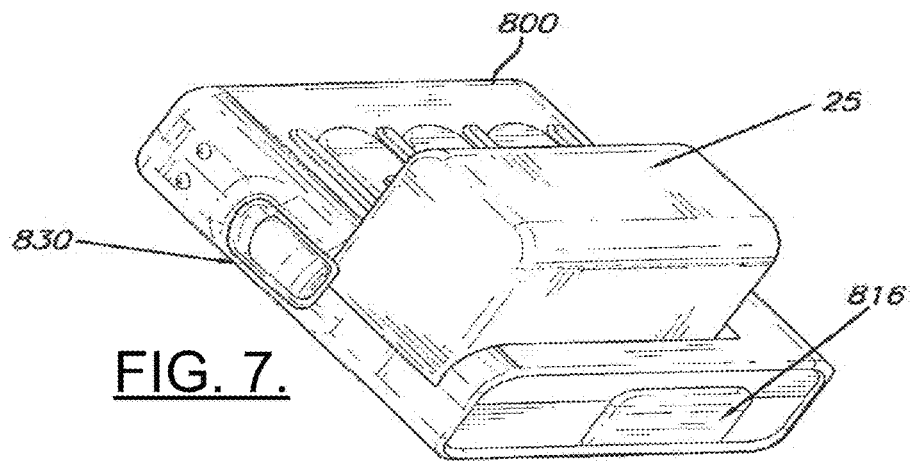
FIGS. 7 and 8 illustrate perspective views of a video processing unit in accordance with an example embodiment.
Figure 8:
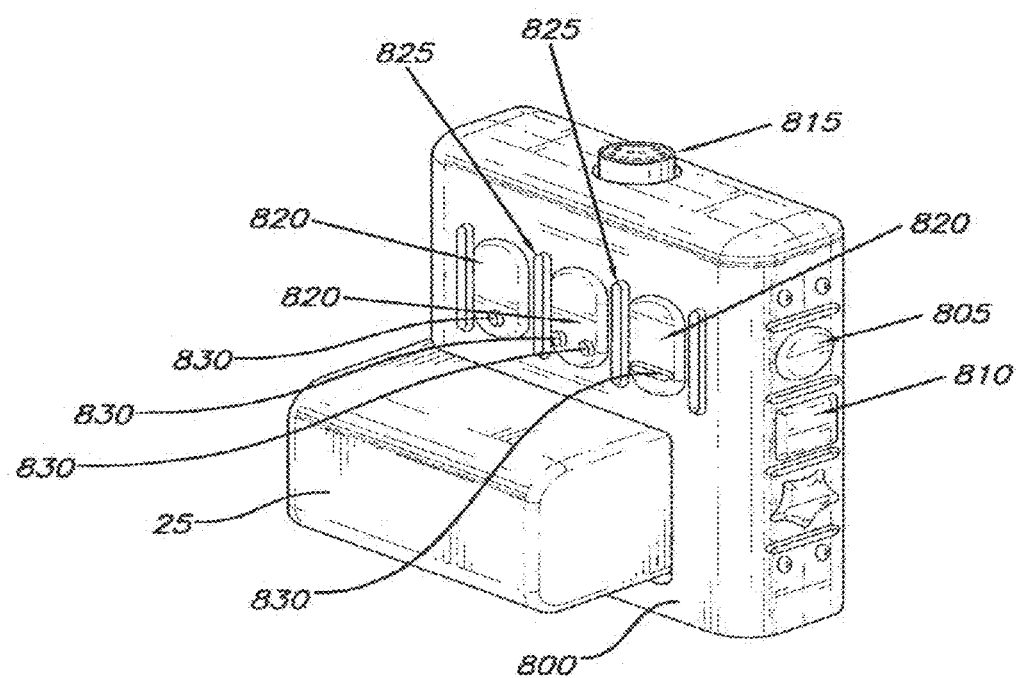

In an example embodiment, the VPU 20 may be configured to allow the subject/patient i) to turn the visual prosthesis apparatus on and off, ii) to manually adjust settings, and iii) to provide power and data to the retinal stimulation system 2000. Referring to FIGS. 7 and 8, the VPU 20 may include a case 800, power button 805 for turning the VPU 20 on and off, setting button 810, zoom buttons 820 for controlling the camera 12, connector port 815 for connecting to the glasses 5, a connector port 816 for connecting to the laptop computer 10 through the connection adapter 40, indicator lights 825 to give visual indication of operating status of the system, the rechargeable battery 25 for powering the VPU 20, battery latch 830 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 8 to help the user identify the functionality of the button without having to look at it. As shown in FIG. 8, the power button 805 may be a circular shape while the settings button 820 may be square shape and the zoom buttons 820 may have special raised markings 830 to also identify the functionality of each respective button. It should be appreciated that other shapes and markings can be used to identify the buttons without departing from the spirit and scope of the disclosed system and methods. For example, the markings can be recessed instead of raised.

In an example embodiment, the indicator lights 825 may indicate that the VPU 20 is going through system start-up diagnostic testing when the one or more indicator lights 825 are blinking fast (more than once per second) and are green in color. The indicator lights 825 may indicate that the VPU 20 is operating normally when the one or more indicator lights 825 are blinking once per second and are green in color. The indicator lights 825 may indicate that the retinal stimulation system 2000 has a problem that was detected by the VPU 20 at start-up diagnostic when the one or more indicator lights 825 are blinking for example once per five second and are green in color. The indicator lights 825 may indicate that the video signal from the camera 12 is not being received by the VPU 20 when the one or more indicator lights 825 are always on and are amber color. The indicator lights 825 may indicate that there is a loss of communication between the retinal stimulation system 2000 and the external coil 14 due to the movement or removal of glasses 5 while the system is operational or if the VPU 20 detects a problem with the retinal stimulation system 2000 and shuts off power to the retinal stimulation system 2000 when the one or more indicator lights 825 are always on and are orange color. It should also be appreciated that other colors and blinking patterns can be used to give visual indication of operating status of the system without departing from the spirit and scope of the disclosed system and methods.

In an example embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As may be appreciated, different periodic beeping may also be used to indicate a low battery voltage warning, that there is a problem with the video signal, and/or there is a loss of communication between the retinal stimulation system 2000 and the external coil 14. It should also be appreciated that other sounds can be used to give audio indication of operating status of the system without departing from the spirit and scope of the disclosed system and methods. For example, the beeps may be replaced by an actual prerecorded voice indicating operating status of the system.

In an example embodiment, the VPU 20 is in constant communication with the retinal stimulation system 2000 through forward and backward telemetry. In this regard, the forward telemetry may refer to transmission from VPU 20 to the retinal stimulation system 2000 and the backward telemetry may refer to transmissions from the retinal stimulation system 2000 to the VPU 20. During the initial setup, the VPU 20 may transmit null frames (containing no stimulation information) until the VPU 20 synchronizes with the retinal stimulation system 2000 via the back telemetry. In one embodiment, an audio alarm may be used to indicate whenever the synchronization has been lost.

In order to supply power and data to the retinal stimulation system 2000, the VPU 20 may drive the external coil 14, for example, with a 3 MHz signal. To protect the subject, the retinal stimulation system 2000 may comprise a failure detection circuit to detect direct current leakage and to notify the VPU 20 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of 10-5 on forward telemetry and 10-3 on back telemetry. These errors may be caught more than 99.998% of the time by both an ASIC hardware telemetry error detection algorithm and the firmware of the VPU 20. For the forward telemetry, this is due to the fact that a 16-bit cyclic redundancy check (CRC) is calculated for every 1024 bits sent to the ASIC within electronics package 2014 of the retinal stimulation system 2000. The ASIC of the retinal stimulation system 2000 verifies this CRC and handles corrupt data by entering a non-stimulating 'safe' state and reporting that a telemetry error was detected to the VPU 20 via back telemetry. During the 'safe' mode, the VPU 20 may attempt to return the implant to an operating state. This recovery may be on the order of milliseconds. The back telemetry words are checked for a 16-bit header and a single parity bit. For further protection against corrupt data being misread, the back telemetry is only checked for header and parity if it is recognized as properly encoded Bi-phase Mark Encoded (BPM) data. If the VPU 20 detects invalid back telemetry data, the VPU 20 immediately changes mode to a 'safe' mode where the retinal stimulation system 2000 is reset and the VPU 20 only sends non-stimulating data frames. Back telemetry errors cannot cause the VPU 20 to do anything that would be unsafe.

Figure 9A:
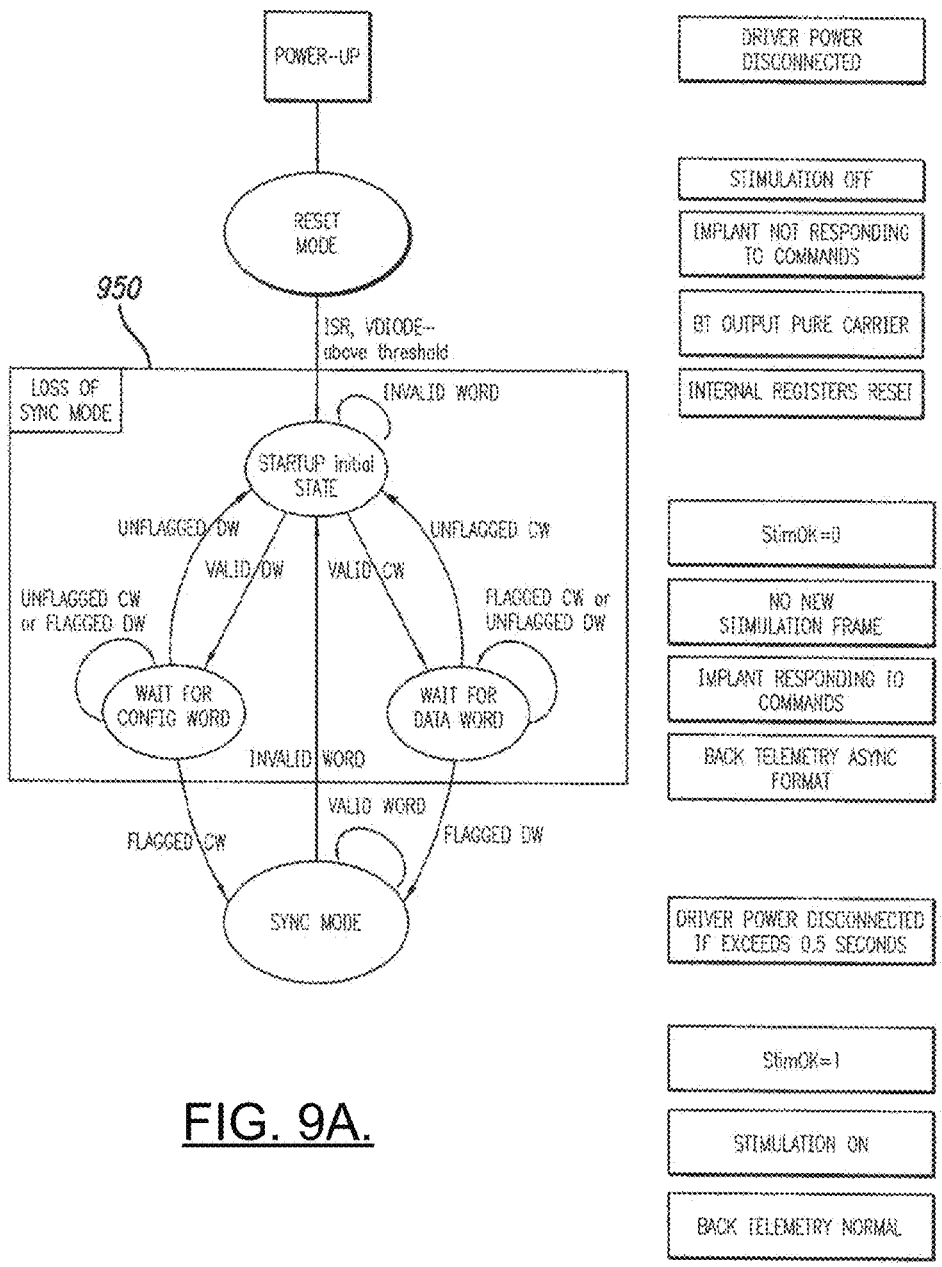
FIG. 9A illustrates a block diagram showing operation in a loss of synch mode in accordance with an example embodiment.

The response to errors detected in data transmitted by VPU 20 may begin at the ASIC of the retinal stimulation system 2000. The retinal stimulation system 2000 may be constantly checking the headers and CRCs of incoming data frames. If either the header or CRC check fails, the ASIC of the retinal stimulation system 2000 may enter a mode called LOSS OF SYNC 950, shown in FIG. 9A. In LOSS OF SYNC mode 950, the retinal stimulation system 2000 will no longer produce a stimulation output, even if commanded to do so by the VPU 20. This cessation of stimulation occurs after the end of the stimulation frame in which the LOSS OF SYNC mode 950 is entered, thus avoiding the possibility of unbalanced pulses not completing stimulation. If the retinal stimulation system 2000 remains in a LOSS OF SYNC mode 950 for 1 second or more (for example, caused by successive errors in data transmitted by VPU 20), the ASIC of the retinal stimulation system 2000 disconnects the power lines to the stimulation pulse drivers. This eliminates the possibility of any leakage from the power supply in a prolonged LOSS OF SYNC mode 950. From the LOSS OF SYNC mode 950, the retinal stimulation system 2000 will not re-enter a stimulating mode until it has been properly initialized with valid data transmitted by the VPU 20.

In addition, the VPU 20 may also take action when notified of the LOSS OF SYNC mode 950. As soon as the retinal stimulation system 2000 enters the LOSS OF SYNC mode 950, the retinal stimulation system 2000 reports this fact to the VPU 20 through back telemetry. When the VPU 20 detects that the retinal stimulation system 2000 is in LOSS OF SYNC mode 950, the VPU 20 may start to send 'safe' data frames to the retinal stimulation system 2000. 'Safe' data is data in which no stimulation output is programmed and the power to the stimulation drivers is also programmed to be off. The VPU 20 will not send data frames to the retinal stimulation system 2000 with stimulation commands until the VPU 20 first receives back telemetry from the retinal stimulation system 2000 indicating that the retinal stimulation system 2000 has exited the LOSS OF SYNC mode 950. After several unsuccessful retries by the VPU 20 to take the implant out of LOSS OF SYNC mode 950, the VPU 20 will enter a Low Power Mode (described below) in which the implant is only powered for a very short time. In this time, the VPU 20 checks the status of the implant. If the implant continues to report a LOSS OF SYNC mode 950, the VPU 20 turns power off to the retinal stimulation system 2000 and tries again later. Since there is no possibility of the implant electronics causing damage when it is not powered, this mode is considered very safe.

Due to an unwanted electromagnetic interference (EMI) or electrostatic discharge (ESD) event the VPU 20 data, specifically the VPU firmware code, in RAM can potentially get corrupted and may cause the VPU 20 firmware to freeze. As a result, the VPU 20 firmware will stop resetting the hardware watchdog circuit, which may cause the system to reset. This will cause the watchdog timer to expire causing a system reset in, for example, less than 2.25 seconds. Upon recovering from the reset, the VPU 20 firmware may log the event and shut itself down. VPU 20 will not allow system usage after this occurs once. This prevents the VPU 20 code from freezing for extended periods of time and hence reduces the probability of the VPU 20 sending invalid data frames to the implant.

Supplying power to the retinal stimulation system 2000 can be a significant portion of the VPU 20's total power consumption. When the retinal stimulation system 2000 is not within receiving range to receive either power or data from the VPU 20, the power used by the VPU 20 is wasted.

Power delivered to the retinal stimulation system 2000 may be dependent on the orientation of the external coil 14 and the secondary coil 2016 (i.e., the internal coil). The power delivered to the retinal stimulation system 2000 may be controlled, for example, via the VPU 20 every 16.6 ms. The retinal stimulation system 2000 may report how much power it receives and the VPU 20 may adjust the power supply voltage of the RF driver to maintain a required power level on the retinal stimulation system 2000. Two types of power loss may occur: 1) long term (>~1 second) and 2) short term (<~1 second). The long term power loss may be caused, for example, by a subject removing the glasses 5.

Figure 9B:
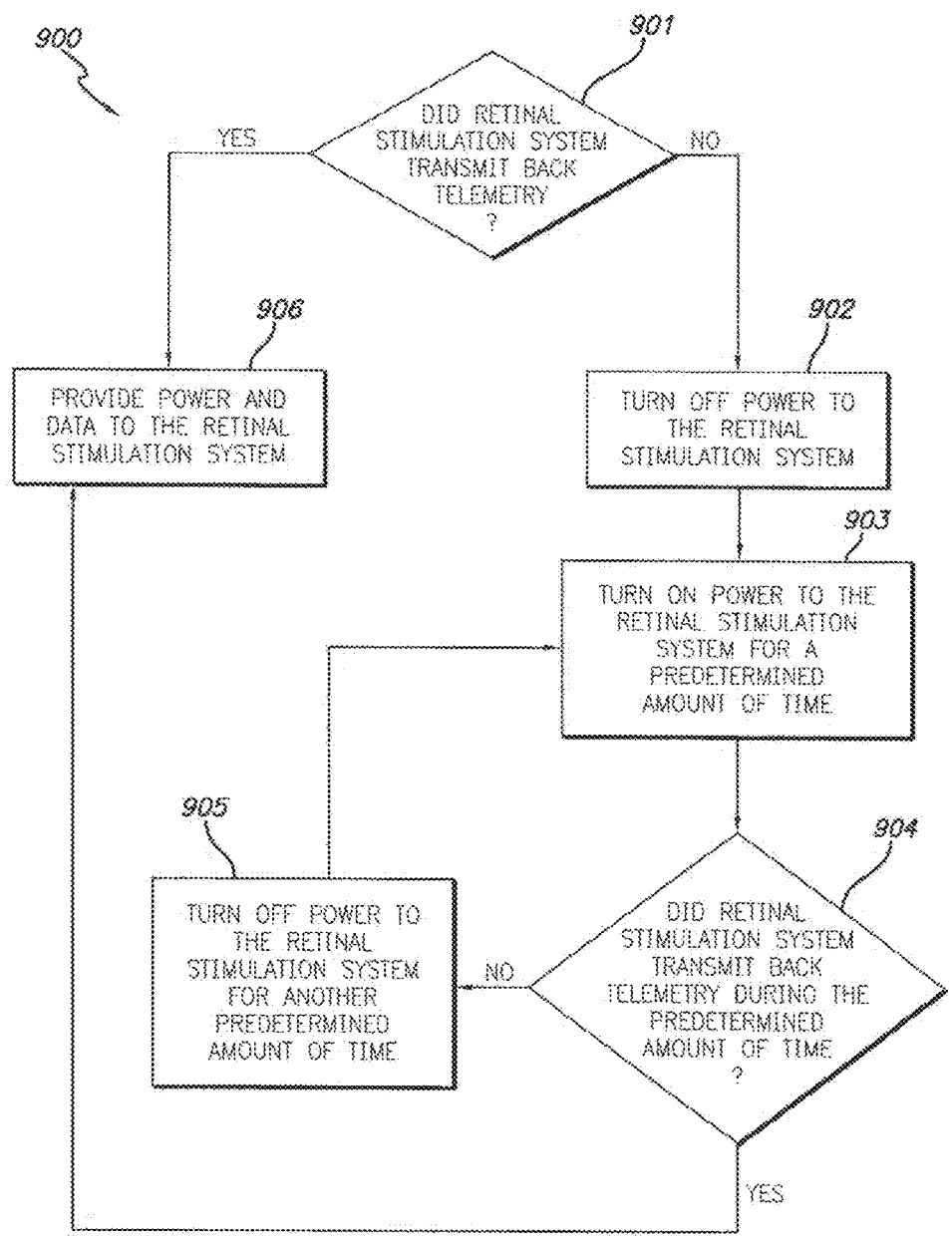
FIG. 9B illustrates a block diagram showing operations performed when the video processing unit does not receive feedback telemetry data from the retinal stimulation system in accordance with an example embodiment.

In an example embodiment, the Low Power Mode may be implemented to save power for VPU 20. The Low Power Mode may be entered, for example, anytime the VPU 20 does not receive back telemetry from the Retinal stimulation system 1. Upon entry to the Low Power Mode, the VPU 20 turns off power to the Retinal stimulation system 1. After that, and periodically, the VPU 20 turns power back on to the retinal stimulation system 2000 for an amount of time just long enough for the presence of the retinal stimulation system 2000 to be recognized via its back telemetry. If the retinal stimulation system 2000 is not immediately recognized, the controller again shuts off power to the retinal stimulation system 2000. In this way, the controller 'polls' for the passive retinal stimulation system 2000 and a significant reduction in power used is seen when the retinal stimulation system 2000 is too far away from its controller device. FIG. 9B depicts an exemplary block diagram 900 of the steps taken when the VPU 20 does not receive back telemetry from the retinal stimulation system 2000. If the VPU 20 receives back telemetry from the retinal stimulation system 2000 (output "YES" of step 901), the retinal stimulation system 2000 may be provided with power and data (step 906). If the VPU 20 does not receive back telemetry from the retinal stimulation system 2000 (output "NO" of step 901), the power to the retinal stimulation system 2000 may be turned off. After some amount of time, power to the retinal stimulation system 2000 may be turned on again for enough time to determine if the retinal stimulation system 2000 is again transmitting back telemetry (step 903). If the retinal stimulation system 2000 is again transmitting back telemetry (step 904), the retinal stimulation system 2000 is provided with power and data (step 906). If the retinal stimulation system 2000 is not transmitting back telemetry (step 904), the power to the retinal stimulation system 2000 may again be turned off for a predetermined amount of time (step 905) and the process may be repeated until the retinal stimulation system 2000 is again transmitting back telemetry.

Figure 9C:
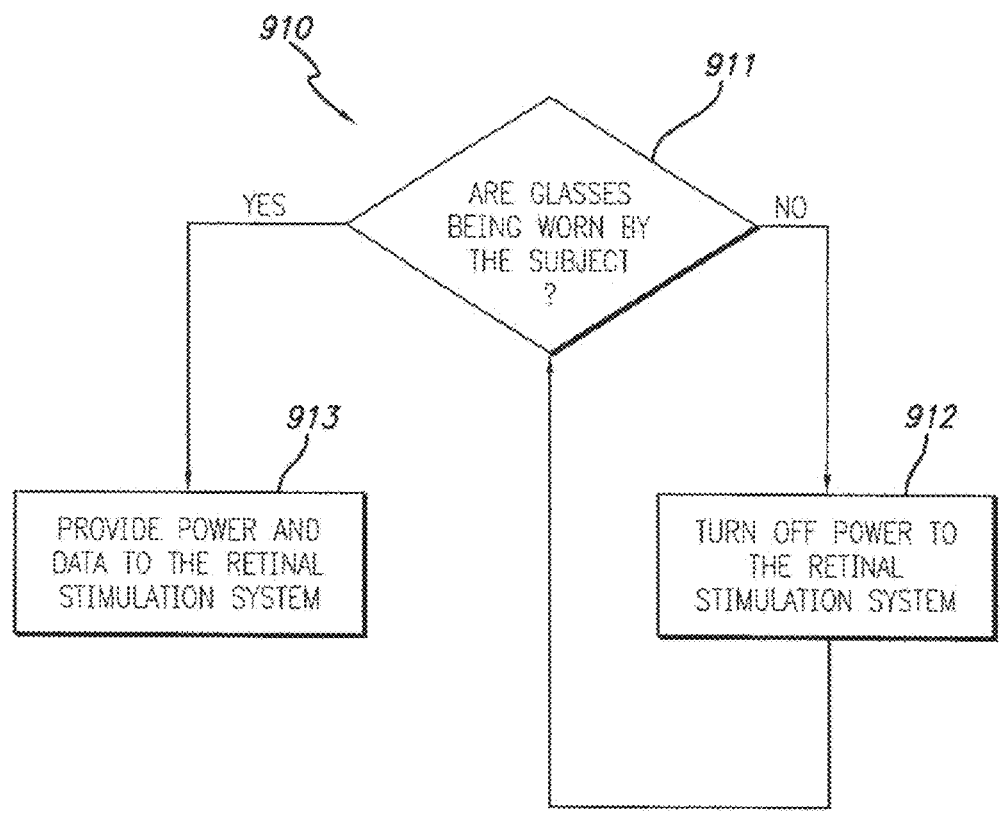
FIG. 9C illustrates a block diagram showing operations for power control responsive to the operator removing glasses in accordance with an example embodiment.
Figure 10A:
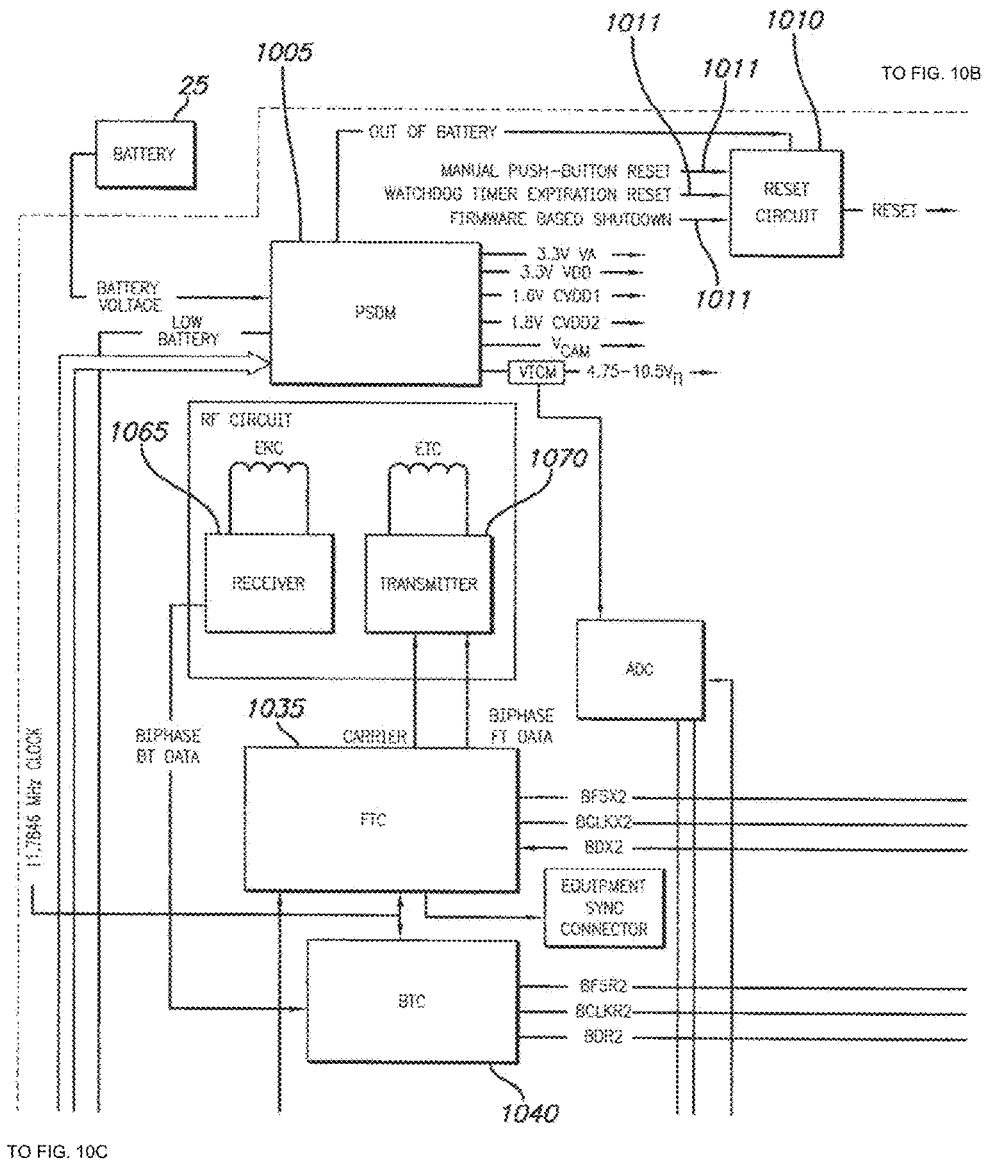
FIGS. 10A, 10B, 10C and 10D illustrate various components of a video processing unit in accordance with an example embodiment.
Figure 10B:
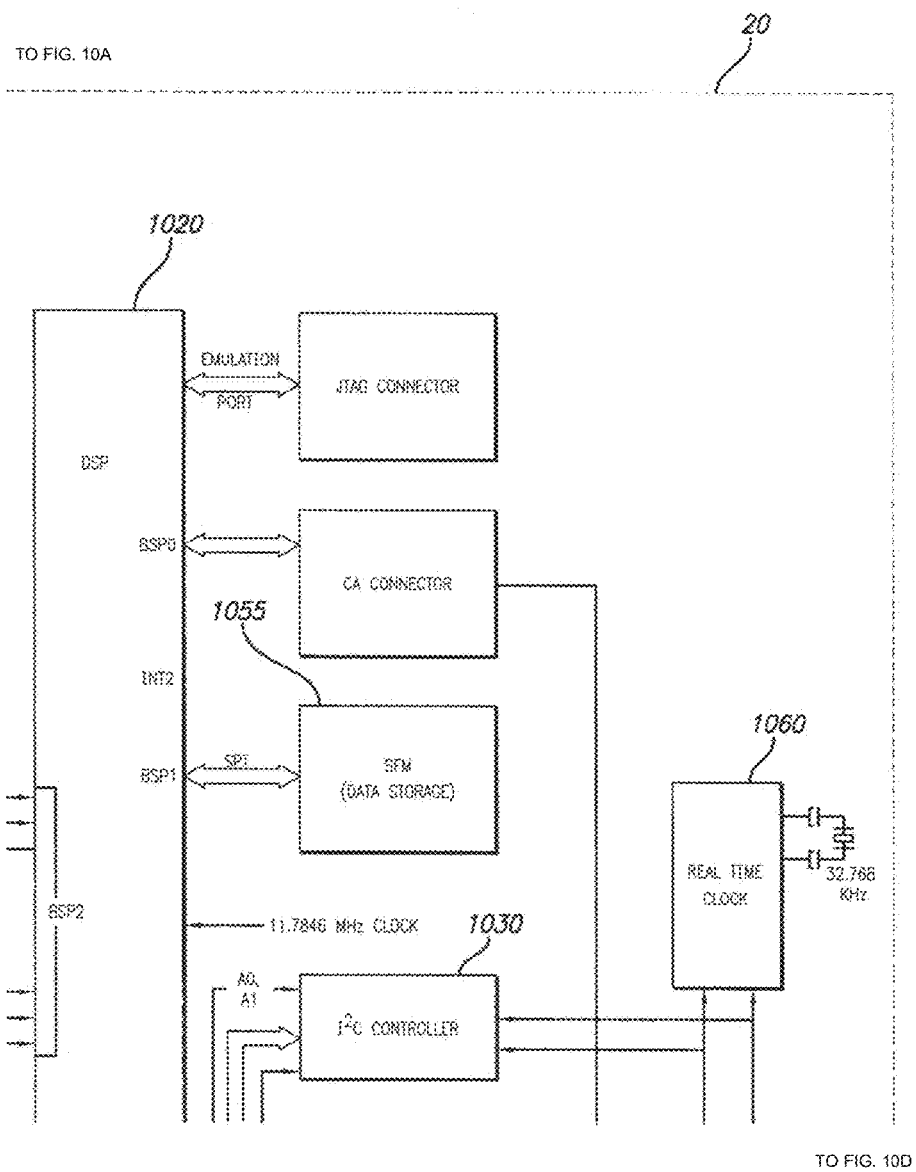
Figure 10C:
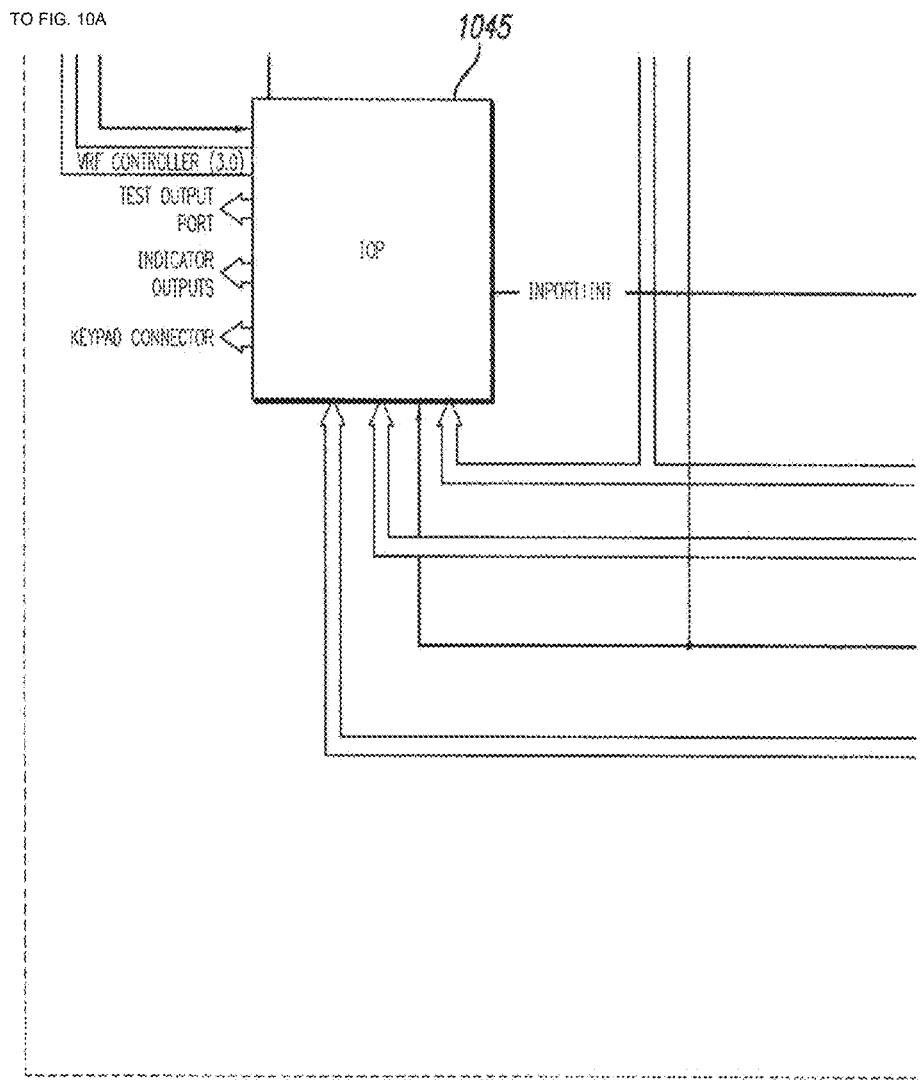
Figure 10D:
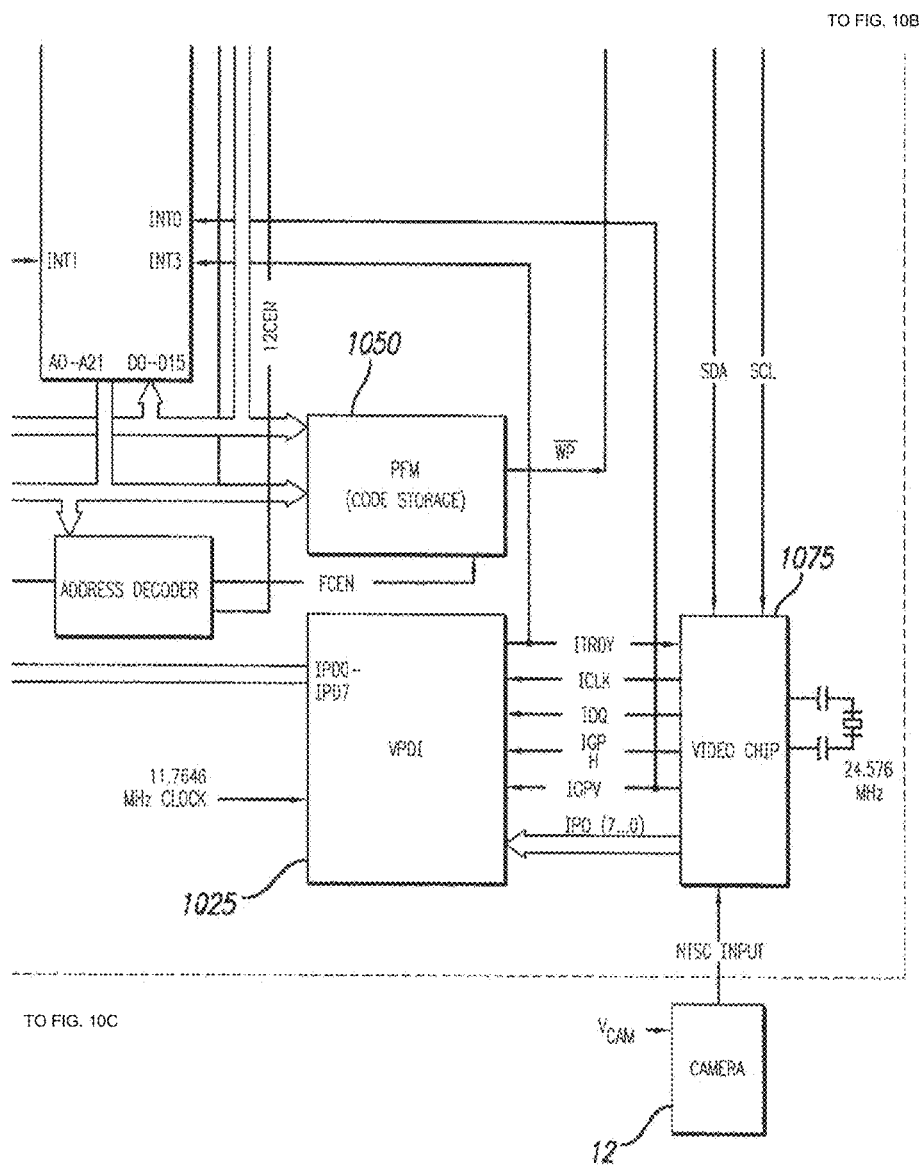

In another example embodiment, the low power mode may be entered whenever the subject is not wearing the glasses 5. In one example, the glasses 5 may contain a capacitive touch sensor (not shown) to provide the VPU 20 with digital information regarding whether or not the glasses 5 are being worn by the subject. In this example, the Low Power Mode may be entered whenever the capacitive touch sensor detects that the subject is not wearing the glasses 5. That is, if the subject removes the glasses 5, the VPU 20 will shut off power to the external coil 14. As soon as the glasses 5 are put back on, the VPU 20 will resume powering the external coil 14. FIG. 9C depicts an example block diagram 910 of the steps taken when the capacitive touch sensor detects that the subject is not wearing the glasses 5. If the subject is wearing glasses 5 (step 911), the retinal stimulation system 2000 is provided with power and data (step 913). If the subject is not wearing glasses 5 (step 911), the power to the retinal stimulation system 2000 is turned off (step 912) and the process is repeated until the subject is wearing the glasses 5.

The VPU 20 can be embodied in a number of different ways. Generally speaking, the VPU 20 may include processing circuitry that can be configured to selectively execute operations in a mode that is either selected by the user or based on environmental context. Additionally or alternatively, the processing circuitry may be configured to execute algorithms for enhancing operation of the system to reduce clutter or improve face detection in the limited resolution context that is provided by the relatively small sized electrode array. FIGS. 10A, 10B, 10C and 10D illustrate one example structural implementation of the VPU 20 according to an example embodiment.

As shown in FIGS. 10A to 10D, the VPU 20 may include: a power supply such as the rechargeable battery 25, a power supply distribution and monitoring (PSDM) circuit 1005, a reset circuit 1010, a system main clock (SMC) source (not shown), a video preprocessor clock (VPC) source (not shown), a digital signal processor (DSP) 1020, video preprocessor data interface 1025, a video preprocessor 1075, an I²C protocol controller 1030, a complex programmable logic device (CPLD) (not shown), a forward telemetry controller (FTC) 1035, a back telemetry controller (BTC) 1040, input/output ports 1045, memory devices like a parallel flash memory (PFM) 1050 and a serial flash memory (SFM) 1055, a real time clock 1060, an RF voltage and current monitoring circuit (VIMC) (not shown), a speaker and/or a buzzer, an RF receiver 1065, and an RF transmitter 1070.

The PSDM circuit 1005 may regulate a variable battery voltage to several stable voltages that apply to components of the VPU 20. The PSDM circuit 1005 may also provide low battery monitoring and depleted battery system cutoff.

The reset circuit 1010 may have reset inputs 1011 that are able to invoke system level rest. For example, the reset inputs 1011 may be from a manual push-button reset, a watchdog timer expiration, and/or firmware based shutdown. The system main clock (SMC) source is a clock source for DSP 1020 and CPLD. The video preprocessor clock (VPC) source is a clock source for the video processor. The DSP 1020 may act as the central processing unit of the VPU 20. The DSP 1020 may communicate with the rest of the components of the VPU 20 through parallel and serial interfaces. The video processor 1075 may convert the NTSC signal from the camera 12 into a down-scaled resolution digital image format. The video processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an analog input processing, chrominance and luminance processing and brightness contrast and saturation (BSC) control circuits. The video scaler may be composed of acquisition control, pre-scaler, BSC-control, line buffer and output interface. The I²C protocol controller 1030 may serve as a link between the DSP 1020 and the I²C bus. The I²C protocol controller 1030 may be able to convert the parallel bus interface of the DSP 1020 to the I²C protocol bus or vice versa. The I²C protocol controller 1030 may also be connected to the video processor 1075 and the real time clock 1060. The VPDI 1025 may contain a tri-state machine to shift video data from video processor 1075 to the DSP 1020. The FTC 1035 packs 1024 bits of forward telemetry data into a forward telemetry frame. The FTC 1035 retrieves the forward telemetry data from the DSP 1020 and converts the data from logic level to biphase marked data. The BTC 1040 retrieves the biphase marked data from the RF receiver 1065, decodes it, and generates the BFSR and BCLKR for the DSP 1020. The input/output ports 1045 provide expanded IO functions to access the CPLD on-chip and off-chip devices. The PFM 1050 may be used to store executable code and the SFM 1055 may provide serial port interface (SPI) for data storage. The VIMC may be used to sample and monitor RF transmitter 1070 current and voltage in order to monitor the integrity status of the retinal stimulation system 2000.

FIG. 11 shows a perspective view of the implanted portion of a visual prosthesis. A flexible circuit associated with the implanted portion of the visual prosthesis may include a flexible circuit electrode array 2010 which is mounted by a retinal tack (not shown) or similar means to the epiretinal surface. The flexible circuit electrode array 2010 is electrically coupled by a flexible circuit cable 2012, which pierces the sclera and is electrically coupled to an electronics package 2014, external to the sclera.

The electronics package 2014 is electrically coupled to a secondary inductive coil (i.e., secondary coil 2016). In some cases, the secondary coil 2016 is made from wound wire. Alternatively, the secondary coil 2016 may be made from a flexible circuit polymer sandwich with wire traces deposited between layers of flexible circuit polymer. The secondary coil 2016 receives power and data from a primary inductive coil 2017, which is external to the body. The electronics package 2014 and secondary coil 2016 may be held together by a molded body 2018. The molded body 2018 holds the electronics package 2014 and secondary coil 2016 end to end. The secondary coil 2016 may be placed around the electronics package 2014 in the molded body 2018. The molded body 2018 may hold the secondary inductive coil 2016 and electronics package 2014 in the end to end orientation and minimize the thickness or height above the sclera of the entire device. The molded body 2018 may also include suture tabs 2020. The molded body 2018 narrows to form a strap 2022 which surrounds the sclera and holds the molded body 2018, secondary inductive coil 2016, and electronics package 2014 in place. The molded body 2018, suture tabs 2020 and strap 2022 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 2016 and molded body 2018 may have an oval shape in some cases since, for example, the strap 2022 can better support an oval shaped coil. It should be noted that the entire implant may be attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package 2014 in an area of fatty tissue between the rectus muscles, eye motion does not cause any flexing which might fatigue, and eventually damage, the device.

Figure 12:
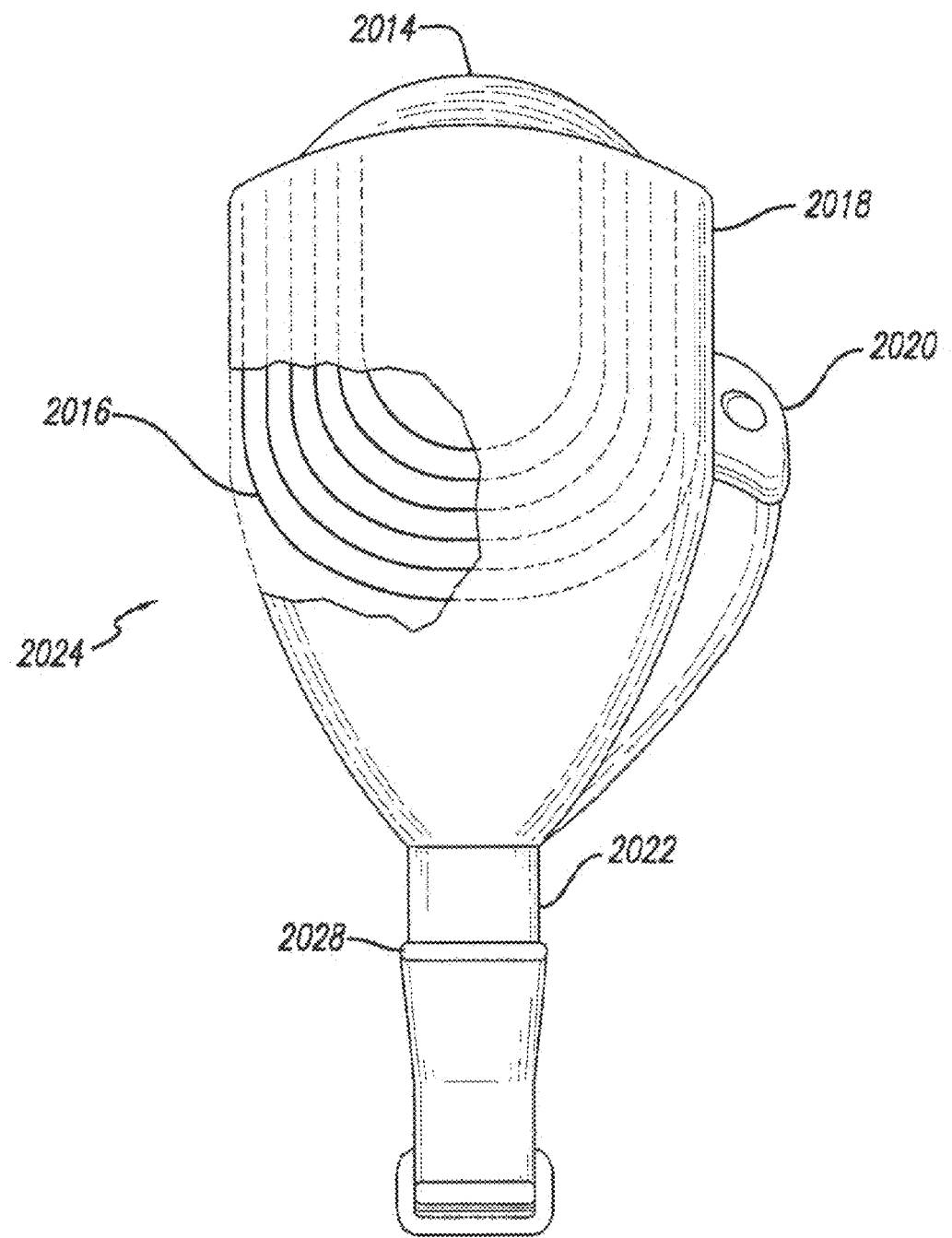
FIG. 12 illustrates a side view of the implanted portion of the visual prosthesis in accordance with an example embodiment.
Figure 13:
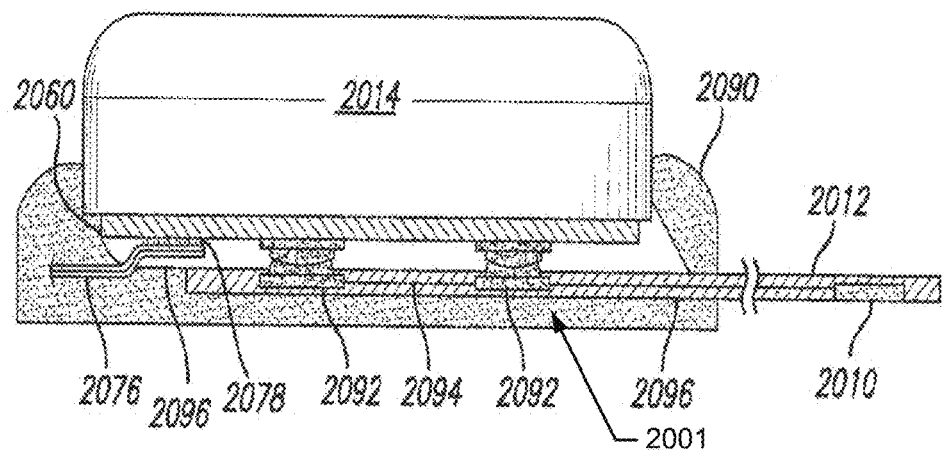
FIG. 13 is a side view of an electronics package for attachment to an electrode array in accordance with an example embodiment.

FIG. 12 shows a side view of the implanted portion of the visual prosthesis, in particular, emphasizing a fan tail 2024. When implanting the visual prosthesis, it may be necessary to pass the strap 2022 under the eye muscles to surround the sclera. The secondary coil 2016 and molded body 2018 may also follow the strap 2022 under the lateral rectus muscle on the side of the sclera. The implanted portion of the visual prosthesis is very delicate. It is easy to tear the molded body 2018 or break wires in the secondary inductive coil 2016. In order to allow the molded body 2018 to slide smoothly under the lateral rectus muscle, the molded body 2018 is shaped in the form of a fan tail 2024 on the end opposite the electronics package 2014. The strap 2022 further includes a hook 2028 that aids the surgeon in passing the strap 2022 under the rectus muscles.

Referring to FIG. 12, the flexible circuit associated with the implanted portion of the visual prosthesis may include platinum conductors 2094 insulated from each other and the external environment by a biocompatible dielectric polymer 2096, e.g., polyimide. One end of the array may have exposed electrode sites that are placed in close proximity to the retinal surface 2010. The other end may include bond pads 2092 that permit electrical connection to the electronics package 2014. The electronic package 2014 may be operably coupled to the flexible circuit using a flip-chip bumping process, and epoxy underfilled. In the flip-chip bumping process, bumps containing conductive adhesive placed on bond pads 2092 and bumps containing conductive adhesive placed on the electronic package 2014 are aligned and melted to build a conductive connection between the bond pads 2092 and the electronic package 2014. Leads 2076 for the secondary inductive coil 2016 are attached to gold pads 2078 on the ceramic substrate 2060 using thermal compression bonding, and are then covered in epoxy. The electrode array cable 2012 is laser welded to the assembly junction and underfilled with epoxy. The junctions of the secondary inductive coil 2016, array 2001, and electronic package 2014 are encapsulated with a silicone overmold 2090 that connects them together mechanically. When assembled, the hermetic electronics package 2014 sits about 3 mm away from the end of the secondary coil 2016.

Since the implant device is implanted just under the conjunctiva, it is possible to irritate or even erode through the conjunctiva. Eroding through the conjunctiva leaves the body open to infection. Several things can be done to lessen the likelihood of conjunctiva irritation or erosion. First, it is important to keep the overall thickness of the implant device to a minimum. Even though it is advantageous to mount both the electronics package 2014 and the secondary coil 2016 on the lateral side of the sclera, the electronics package 2014 is mounted higher than, but not covering, the secondary coil 2016. In other words, the thickness of the secondary coil 2016 and electronics package 2014 should not be cumulative.

It may also be advantageous to place protective material between the implant device and the conjunctiva. This is particularly important at the scleratomy, where the thin film electrode array cable 2012 penetrates the sclera. The thin film electrode array cable 2012 must penetrate the sclera through the pars plana, not the retina. The scleratomy is, therefore, the point where the implant device comes closest to the conjunctiva. The protective material can be provided as a flap attached to the implant device or a separate piece placed by the surgeon at the time of implantation. Further material over the scleratomy will promote healing and sealing of the scleratomy. Suitable materials include DACRON®, TEFLON®, GORETEX® (ePTFE), TUTOPLAST® (sterilized sclera), MERSILENE® (polyester) or silicone.

Figure 14:
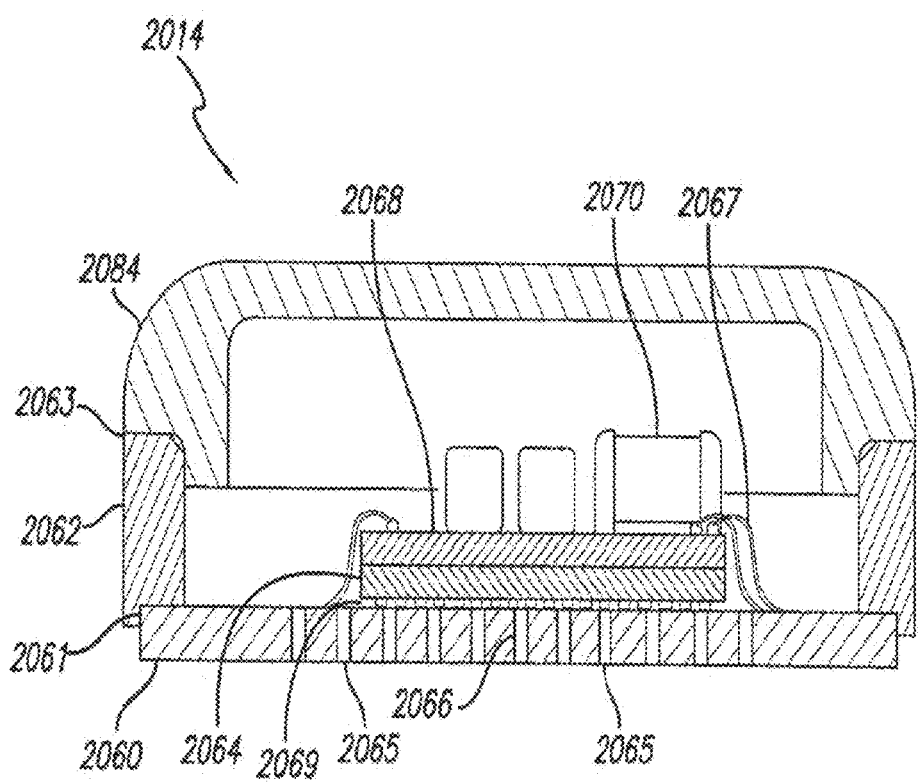
FIG. 14 is a cross section view of the electronics package of FIG. 12 in accordance with an example embodiment.

Referring to FIG. 14, the electronics package 2014 may include a ceramic substrate 2060, with metalized vias 2065 and thin-film metallization 2066. The electronics package 2014 may also include a metal case wall 2062, which may be operably coupled to the ceramic substrate 2060 by braze joint 2061. On the ceramic substrate 2060, an underfill 2069 may be applied. On the underfill 2069, an integrated circuit chip 2064 may be positioned. On the integrated circuit chip 2064, a ceramic hybrid substrate 2068 may be positioned. On the ceramic hybrid substrate 2068, passives 2070 may be placed. Wirebonds 2067 may lead from the ceramic substrate 2060 to the ceramic hybrid substrate 2068. A metal lid 2084 may be operably coupled to the metal case wall 2062 by laser welded joint 2063 whereby the electronics package 2014 is sealed.

Figure 15:
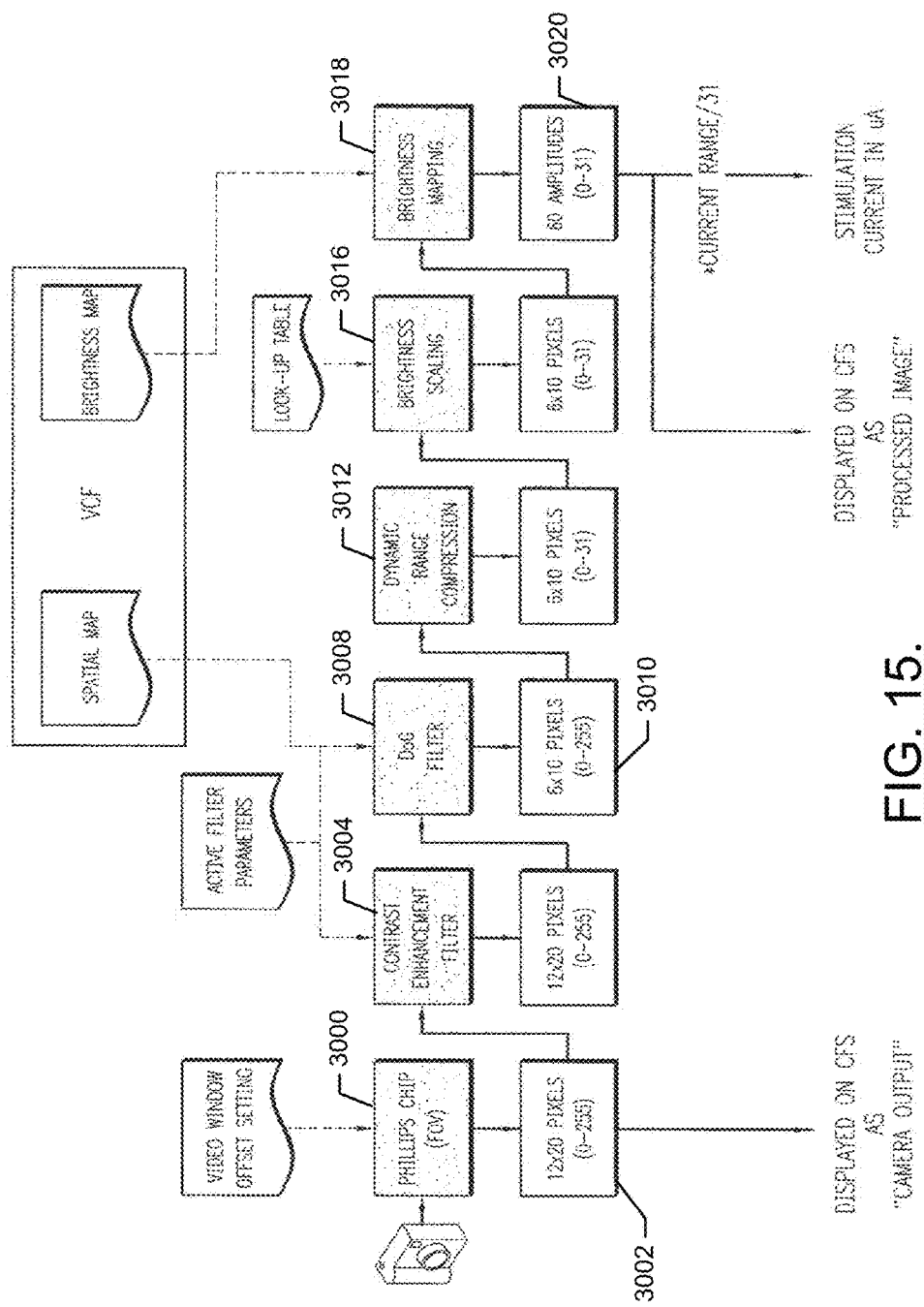
FIG. 15 is a block diagram of a video processing chain that can be executed for the visual prosthesis in accordance with an example embodiment.

FIG. 15 illustrates a block diagram of video chain processing according to an example embodiment. As shown in FIG. 15, a camera image may initially be received in a defined FOV at operation 3000. A defined number of pixels may then be presented with corresponding grayscale values at operation 3002 as a camera output. The image may be contrast enhanced via a contrast enhancement filter 3004. A difference of Gaussians filter 3008 may be applied and the pixel count may be reduced in size for fitting the electrode array of the implant at operation 3010. At operation 3012, dynamic range compression may be employed followed by brightness scaling 3016 and brightness mapping 3018 before the amplitudes of all 60 electrodes of the electrode array can be determined at operation 3020 to generate stimulation current and a processed image.

Accordingly, the examples described above may provide an improved visual prosthesis and an improved method for limiting power consumption in a visual prosthesis. While systems and methods for clutter reduction and face detection for a visual prosthesis have been described by means of specific embodiments and applications thereof, it is understood that numerous modifications and variations could be made thereto by those skilled in the art without departing from the spirit and scope thereof. It is therefore to be understood that the system and methods disclosed herein may be practiced otherwise than as specifically described herein without departing from the scope of the system and methods.

Example embodiments may address two fundamental needs for blind individuals using existing retinal prosthetic devices, namely the ability to identify objects in cluttered backgrounds as well as to identify faces in the scene. Example embodiments provide optimization strategies necessary to allow these algorithms to run in real-time on low power, embedded devices as found in the existing ARGUS® II System or similar systems.

However, as described above, even though improved algorithms have been developed, and may continue to be developed, to enable blind individuals to get improved performance from retinal prosthetic devices, it should be appreciated that sighted individuals working to develop such algorithms may face struggles in conducting effective testing of improvements. Accordingly, it may be desirable to provide a platform that can simulate a retinal prosthesis to enable presentation of the results of algorithms or other image processing techniques to sighted individuals as live video.

FIG. 16 is a block diagram of a development tool for simulating a retinal prosthesis in accordance with an example embodiment. The tool includes an outward facing camera 5000 that may be aimed in front of the wearer to capture image data from an external scene 5010 with a relatively wide field of view. The image data may then be processed via a vision algorithm 5020. The vision algorithm 5020 may include any of the image processing algorithms or other techniques described herein, or other image processing techniques that are tested or developed. As such, for example, the vision algorithm 5020 may be an algorithm or processing technique whose efficacy is being tested.

The results of the vision algorithm 5020 may be cropped to the effective field of view of the implant (e.g., the implant FOV 210) and downsampled to the effective resolution and dynamic range of the implant. The result may be a low resolution image (e.g., a 6×10 pixel image) that is then upsampled and blurred 5030 so that an image can be provided to a head mounted display 5040 that approximates what a wearer of a visual prosthesis (e.g., as shown in FIG. 11) would see via the processing provided by the vision algorithm 5020 (i.e., the algorithm or processing technique under test).

The tool may further include an inward facing camera 5050 that is aimed at the eye 5060 of the wearer. The inward facing camera 5050 is used to track the pupil of the eye 5060 of the wearer. In particular, a gaze tracker 5070 may be configured to track movement of the pupil to determine which part of the external scene should be displayed in the center of the head mounted display 5040. Thus, for example, the gaze tracker 5070 may enable selection of a region of interest 5080 that corresponds to the portion of the external scene (or video image thereof) that is the focus of the wearer's gaze. The region of interest may then define which portion of image data should be cropped, and the remaining portion after cropping (of the image data processed by the vision algorithm 5020) can be upsampled and blurred 5030 before presentation at the head mounted display 5040.

The outward facing camera 5000 and the inward facing camera 5050 may each be mounted, for example, on a pair of glasses (similar to the glasses 5 above). Processing circuitry may then be provided in a VPU that is separate from the glasses, and operably coupled thereto wirelessly or by a cable, or the VPU may also be mounted on the glasses.

FIG. 17 illustrates a block diagram showing components of an apparatus 6000 used for providing the tool of FIG. 16. As shown in FIG. 17, the apparatus 6000 may include or otherwise be in communication with processing circuitry 6150 that is configured to perform data processing, application execution and other processing and management services according to an example embodiment of the present invention. In one embodiment, the processing circuitry 6150 may include a storage device 6154 and a processor 6152 that may be in communication with or otherwise control the gaze tracker 5070, an ROI selector 6200, an upsampling and blurring engine 6300 and a device interface 6400. As such, the processing circuitry 6150 may be embodied as a circuit chip (e.g., an integrated circuit chip) configured (e.g., with hardware, software or a combination of hardware and software) to perform operations described herein. However, in some embodiments, the processing circuitry 6150 may be embodied as a portion of a computing device mountable on the glasses or capable of operable coupling to the glasses.

The device interface 6400 may include one or more interface mechanisms for enabling communication with or between, components, devices and/or the like. In some cases, the device interface 6400 may be any means such as a device or circuitry embodied in either hardware, software, or a combination of hardware and software that is configured to receive and/or transmit data from/to a component and/or any other device or module in communication with the processing circuitry 6150. In this regard, the device interface 6400 may include, for example, hardware and/or software for enabling communications with a wireless communication network and/or a communication modem or other hardware/software for supporting communication via cable, digital subscriber line (DSL), universal serial bus (USB), Ethernet or other methods. In situations where the device interface 6400 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 6154 may include one or more non-transitory storage or memory devices such as, for example, volatile and/or non-volatile memory that may be either fixed or removable. The storage device 6154 may be configured to store information, data, applications, instructions or the like for enabling the apparatus to carry out various functions in accordance with example embodiments of the present invention. For example, the storage device 6154 could be configured to buffer input data for processing by the processor 6152. Additionally or alternatively, the storage device 6154 could be configured to store instructions for execution by the processor 6152. As yet another alternative, the storage device 6154 may include one of a plurality of databases that may store a variety of files, policies, instructions, contents or data sets. Among the contents of the storage device 6154, applications may be stored for execution by the processor 6152 in order to carry out the functionality associated with each respective application. The applications may, for example, instruct the processor 6152 to execute algorithms or image processing techniques as described herein.

The processor 6152 may be embodied in a number of different ways. For example, the processor 6152 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 6152 may be configured to execute instructions stored in the storage device 6154 or otherwise accessible to the processor 6152. As such, whether configured by hardware or software methods, or by a combination thereof, the processor 6152 may represent an entity (e.g., physically embodied in circuitry) capable of performing operations according to embodiments of the present invention while configured accordingly. Thus, for example, when the processor 6152 is embodied as an ASIC, FPGA or the like, the processor 6152 may be specifically configured hardware for conducting the operations described herein. Alternatively, as another example, when the processor 6152 is embodied as an executor of software instructions, the instructions may specifically configure the processor 6152 to perform the operations described herein.

In an example embodiment, the processor 6152 (or the processing circuitry 6150) may be embodied as, include or otherwise control the gaze tracker 5070, the ROI selector 6200, the upsampling and blurring engine 6300, each of which may each be any means such as a device or circuitry operating in accordance with software or otherwise embodied in hardware or a combination of hardware and software (e.g., processor 6152 operating under software control, the processor 6152 embodied as an ASIC or FPGA specifically configured to perform the operations described herein, or a combination thereof) thereby configuring the device or circuitry to perform the corresponding functions of the gaze tracker 5070, the ROI selector 6200, the upsampling and blurring engine 6300, respectively, as described herein.

In some cases, example embodiments may employ visual simultaneous localization and mapping (SLAM) techniques by leveraging a three dimensional vision sensor, an inertial measurement unit (IMU) and perception algorithms to extract features in real time and detect salient features, words or images in a scene (e.g., restroom, exit, office door signs, etc.). Processing circuitry may be employed to build a map and localize the patient or subject using the prosthetic vision system described herein. Once the map is built of the unstructured environment, the salient features can be represented and the patient or subject may further be enabled to query recorded landmarks. The patient or subject may then be presented with navigational cues to find any selected or desired landmark or other salient feature.

The map may be continuously developed, and various methods may be employed to limit storage requirements. For example, internal cues, such as determining that the patient or subject has left the building (e.g., by identifying trees, clouds, external doors, changes in lighting, or other objects that would only appear outside). In other alternatives, time expiration or geographic distance thresholds may be employed to limit storage requirements. GPS may be used, with or without IMU, depending upon the availability of each. For example, IMU may be preferred in doors, and may be used in conjunction with image processing to register features to extract location information.

In some cases, sift/surf features may be employed to detect a variety of signs and other objects in a scene. Deep learning techniques may also be leveraged in some embodiments where it is possible to download a pre-trained classifier onto existing hardware to find and localize signs or other features. The use of augmented reality techniques such as bar codes and/or markers may be employed as well, in some cases. In some embodiments, cloud based services may allow virtual tours of places with publicly available localization information and image data (e.g., museums, etc.). If image data is available beforehand, the image data could also be used to help build the map. In any case, the wearer may be enabled to provide a query or other input selecting a desired landmark (or particular object). If the particular object can be located within the camera FOV, then the wearer may be provided with spatial cues to indicate a relative location of the particular object to enable the wearer to bring the particular object into the implant FOV. Thus, example embodiments can provide spatial cues to enable the wearer to bring a particular object, such as a face generally, or an object, a sign, a landmark, or even a specific face that the wearer can select, into the implant FOV.

FIG. 18 illustrates an example apparatus 7000 for employing SLAM techniques as described herein. The apparatus 7000 may include a device interface 7400 and processing circuitry 7150 that may further include a storage device 7154 and a processor 7152 that may be similar in form and/or function to those components described above in connection with FIG. 17. The processing circuitry 7000 may also be in communication with or otherwise control a vision sensor 7200, a positioning module 7250, a feature extractor 7300 and a mapping agent 7350 that may be configured to perform the corresponding functions described above.

As may be appreciated from the descriptions herein, some example embodiments may be practiced using an apparatus such as those described in reference to the FIGS. discussed above. The apparatus may improve performance of a retinal implant using specially configured processing circuitry. The processing circuitry may be configured to receive image data corresponding to a camera field of view, determine whether a particular object is detected within the camera field of view, perform image data processing to enable a representation of a portion of the image data corresponding to an implant field of view to be provided on a retinal implant where the implant field of view is smaller than the camera field of view, and, responsive to the particular object being located outside the implant field of view, provide a directional indicator in the implant field of view to indicate a location of the particular object relative to the implant field of view.

In some cases, the system or apparatuses described above may also be modified, augmented or amplified in some cases. For example, in some cases, the directional indicator may employ a selected indication paradigm (e.g., pre-programmed, or selected by the wearer). In an example embodiment, the selected indication paradigm may be identified by a characteristic of the directional indicator that indicates a type of spatial cue provided by the directional indicator. For example, the characteristic may be a size, shape, intensity, blink pattern, blink frequency, or display pattern of the directional indicator as presented on the electrodes of the implant. In some example embodiments, the selected indication paradigm may indicate a direction (e.g., a relative direction) outside the implant at which the particular object can be found. Alternatively or additionally, the selected indication paradigm may indicate a location of the particular object relative to the camera field of view (i.e., indicating, on the implant field of view, where in the camera field of view, the particular object is located). In an example embodiment, the directional indicator may be overlaid over other image data (e.g., representation of a face) in the implant field of view. In some examples, the apparatus further includes a video processing unit having the processing circuitry. In such examples, the video processing unit may be operably coupled to glasses including a camera defining the camera field of view. Moreover, in such examples, the video processing unit may be operably coupled to the retinal implant, where the retinal implant is defined by a 10×6 electrode array. Additionally or alternatively, the video processing unit may be configured to transition to a low power mode responsive to an indication that the glasses are not being worn by a user. Additionally or alternatively, the particular object may be a face, and the video processing unit may be configured to transition between a face detection mode and a background clutter reduction mode based on detection of the face in the camera field of view. In such an example, the video processing unit may be configured to determine whether the face is in the implant field of view, and perform segmentation of the image data around the face in response to the face being in the implant field of view. In some examples, the segmentation may include defining an ellipse around the face, and the video processing unit may be configured to perform image enhancement inside the ellipse and perform filtering on background data outside the ellipse. In an example embodiment, the video processing unit may be further configured to downsample an output from the image enhancement prior to display at the retinal implant. In some example embodiments, the video processing unit may be configured to determine that the face is no longer in the field of view and continue to display the face for at least a predetermined time thereafter. In an example embodiment, the apparatus may further include a mapping agent and a positioning module. The mapping agent may be configured to construct a map and the positioning module may determine location information relative to the map. In such an example, the processing circuitry may be configured to receive a query regarding the particular object from a wearer of the apparatus. In such an example, the processing circuitry may be further configured to provide the directional indicator in the implant field of view to indicate the location of the particular object relative to the implant field of view. In some examples, the particular object is an object, landmark, sign, or specific face selected by the wearer.

As mentioned above, when not in the face detection mode, the processing circuitry may be provided in a clutter reduction mode. The clutter reduction mode can operate on a live video feed from a head-mounted camera. The clutter reduction mode can be implemented using image processing techniques (or algorithms) that configure the image data specifically for optimal presentation on the retinal implant. In this regard, for example, the image processing technique or algorithm may reduce the amount of information in the scene by utilizing K-means to cluster pixels into a fixed number of bins. These bins may then be scaled to increase contrast and a grayscale image may be output with a smaller, fixed number of different intensities. The image may then be cropped, resized, and fed to the prosthetic device.

As an alternative to the K-means clustering, some example embodiments may employ means shift. Means shift may work to cluster neighborhoods of pixels with similar color and intensity properties. Such clustering may effectively reduce the number of unique pixel values and simplify the image. The new clustered color image (as simplified by means shift) may then be converted to grayscale, cropped, resized, and fed to the prosthetic device. The smaller electrode array of the prosthetic device can then display an optimally processed image for the subject or wearer of the prosthetic device.

In still other examples embodiments, a development tool may be provided to enable sighted individuals to experience the view provided by the retinal implant so that various vision algorithms may be tested for efficacy. The development tool may include a forward facing camera having image data processed as described above. As such, the image data may be processed by techniques or algorithms for reducing the size of the image date for optimal presentation on the relatively small electrode array of the retinal implant. However, the tool may also include a camera that faces toward the wearer's eye to track the gaze of the wearer relative to the camera field of view and define a region of interest within the processed image data based on the wearer's gaze. The results of the processed image data may be formatted for provision to the retinal implant (e.g., as a 10×6 image). Thus, the tool may be configured to upsample and blur the image before the image is presented to a head mounted display worn by the wearer. The image presented in the head mounted display may approximate that which would be experienced by an individual having the retinal implant. Accordingly, a sighted individual can experience the output of the technique or algorithm being employed for processing and reducing the image data gathered by the outward facing camera. As such, various different algorithms can be tested by sighted individuals.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. An apparatus comprising:
a video processing unit operably coupled to a camera defining a camera field of view, the video processing unit including processing circuitry, the processing circuitry being configured to:
receive image data corresponding to the camera field of view;
determine whether a particular object is detected within the camera field of view, wherein the particular object comprises a face;
perform image data processing to enable a representation of a portion of the image data corresponding to an implant field of view to be provided on a retinal implant, the implant field of view being smaller than the camera field of view; and
responsive to the particular object being located outside the implant field of view, provide a directional indicator in the implant field of view to indicate a location of the particular object relative to the implant field of view, wherein the video processing unit is configured to transition between a face detection mode and a background clutter reduction mode based on detection of the face in the camera field of view.

2. The apparatus of claim 1, wherein the directional indicator employs a selected indication paradigm.

3. The apparatus of claim 2, wherein the selected indication paradigm is identified by a characteristic of the directional indicator that indicates a type of spatial cue provided by the directional indicator.

4. The apparatus of claim 3, wherein the characteristic comprises a size, shape, intensity, blink pattern, blink frequency, or display pattern of the directional indicator.

5. The apparatus of claim 2, wherein the selected indication paradigm indicates a direction outside the implant at which the particular object can be found.

6. The apparatus of claim 2, wherein the selected indication paradigm indicates a location of the particular object relative to the camera field of view.

7. The apparatus of claim 1, wherein the directional indicator is overlaid over other image data in the implant field of view.

8. The apparatus of claim 1, wherein the video processing unit is operably coupled to glasses.

9. The apparatus of claim 1, wherein the video processing unit is operably coupled to the retinal implant, the retinal implant being defined by an electrode array.

10. The apparatus of claim 1, wherein the video processing unit is configured to determine whether the face is in the implant field of view, and perform segmentation of the image data around the face in response to the face being in the implant field of view.

11. The apparatus of claim 10, wherein the segmentation comprises defining a shape around the face, and wherein the video processing unit is configured to perform image enhancement inside the shape and perform filtering on background data outside the ellipse.

12. The apparatus of claim 11, wherein the image enhancement comprises histogram equalization, intensity adjustment, or contrast adjustment.

13. The apparatus of claim 11, wherein the video processing unit is further configured to downsample an output from the image enhancement prior to display at the retinal implant.

14. The apparatus of claim 10, wherein the video processing unit is configured to determine that the face is no longer in the field of view and continue to display the face for at least a predetermined time.

15. The apparatus of claim 1, further comprising a mapping agent and a positioning module, wherein the mapping agent constructs a map and the positioning module determines location information relative to the map.

16. The apparatus of claim 15, wherein the processing circuitry is configured to receive a query regarding the particular object from a wearer of the apparatus, and wherein the processing circuitry is further configured to provide the directional indicator in the implant field of view to indicate the location of the particular object relative to the implant field of view.

17. The apparatus of claim 16, wherein the particular object is a specific face selected by the wearer.

18. A method comprising:
  receiving, by processing circuitry, image data corresponding to a camera field of view, wherein the processing circuitry is part of a video processing unit that is operably coupled to a camera defining the camera field of view;
  determining, by the processing circuitry, whether a face is detected within the camera field of view;
  performing, by the processing circuitry, image data processing to enable a representation of a portion of the image data corresponding to an implant field of view to be provided on a retinal implant, the implant field of view being smaller than the camera field of view;
  providing, by the processing circuitry and responsive to the face being located outside the implant field of view, a directional indicator in the implant field of view to indicate a location of the face relative to the implant field of view; and
  transitioning, by the video processing unit, between a face detection mode and a background clutter reduction mode based on detection of the face in the camera field of view.

* * * * *